(12) United States Patent
Donner et al.

(10) Patent No.: US 11,617,654 B2
(45) Date of Patent: Apr. 4, 2023

(54) ARCUATE FIXATION MEMBER

(71) Applicant: DePuy Synthes Products, Inc., Raynham, MA (US)

(72) Inventors: Thomas Donner, Thibodaux, LA (US); Jared Schoenly, Spring City, PA (US); David E. Evans, Atlanta, GA (US); Andreas Gfeller, Zofingen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/032,016

(22) Filed: Sep. 25, 2020

(65) Prior Publication Data

US 2021/0015624 A1    Jan. 21, 2021

Related U.S. Application Data

(63) Continuation of application No. 15/898,991, filed on Feb. 19, 2018, now Pat. No. 10,806,592, which is a
(Continued)

(51) Int. Cl.
*A61F 2/44* (2006.01)
*A61F 2/46* (2006.01)
(Continued)

(52) U.S. Cl.
CPC .............. *A61F 2/442* (2013.01); *A61B 17/70* (2013.01); *A61B 17/7056* (2013.01);
(Continued)

(58) Field of Classification Search
CPC ...... A61F 2/442; A61F 2/4455; A61F 2/4465; A61F 2/4611; A61B 17/70; A61B 17/68;
(Continued)

(56) References Cited

U.S. PATENT DOCUMENTS 2,916,956 A    12/1959  Salomon
2,984,949 A    5/1961   Dayton et al.
(Continued)

FOREIGN PATENT DOCUMENTS

CA    2279936 A1    8/1998
CA    2279938 C     1/2006
(Continued)

OTHER PUBLICATIONS

International Patent Application No. PCT/US2010/031244: International Search Report dated Nov. 3, 2010, 10 pages.
(Continued)

*Primary Examiner* — Jessica Weiss
(74) *Attorney, Agent, or Firm* — BakerHostetler

(57) ABSTRACT

Arcuate fixation members with varying configurations and/or features are provided, along with additional components for use therewith in provided intervertebral implants. The arcuate fixation members may be of different lengths, cross sectional geometries, and/or cross sectional areas. Applications of intervertebral implants utilizing arcuate fixation members are particularly suitable when a linear line-of-approach for delivering fixation members is undesirable.

19 Claims, 18 Drawing Sheets

Related U.S. Application Data continuation of application No. 15/060,566, filed on Mar. 3, 2016, now Pat. No. 9,925,056, which is a continuation of application No. 14/148,949, filed on Jan. 7, 2014, now Pat. No. 9,445,913, which is a continuation of application No. 13/070,883, filed on Mar. 24, 2011, now Pat. No. 8,641,766, which is a continuation-in-part of application No. 12/761,101, filed on Apr. 15, 2010, now Pat. No. 9,408,715.

(60) Provisional application No. 61/169,461, filed on Apr. 15, 2009.

(51) Int. Cl.
*A61B 17/70* (2006.01)
*A61B 17/92* (2006.01)
*A61B 17/84* (2006.01)
A61B 17/86 (2006.01)
A61F 2/28 (2006.01)
A61F 2/30 (2006.01)

(52) U.S. Cl.
CPC ............ *A61B 17/846* (2013.01); *A61B 17/92* (2013.01); *A61F 2/4455* (2013.01); *A61F 2/4465* (2013.01); *A61F 2/4611* (2013.01); A61B 2017/8655 (2013.01); A61F 2/28 (2013.01); A61F 2/30744 (2013.01); A61F 2/30965 (2013.01); A61F 2002/2835 (2013.01); A61F 2002/30387 (2013.01); A61F 2002/30507 (2013.01); A61F 2002/30514 (2013.01); A61F 2002/30517 (2013.01); A61F 2002/30578 (2013.01); A61F 2002/30593 (2013.01); A61F 2002/30604 (2013.01); A61F 2002/30616 (2013.01); A61F 2002/30777 (2013.01); A61F 2002/30784 (2013.01); A61F 2002/30787 (2013.01); A61F 2002/30841 (2013.01); A61F 2002/30843 (2013.01); A61F 2002/30845 (2013.01); A61F 2002/4627 (2013.01); A61F 2002/4628 (2013.01); A61F 2220/0016 (2013.01); A61F 2220/0025 (2013.01); A61F 2310/00017 (2013.01); A61F 2310/00023 (2013.01); A61F 2310/00131 (2013.01); A61F 2310/00359 (2013.01)

(58) Field of Classification Search
CPC ... A61B 17/7056; A61B 17/846; A61B 17/92; A61B 17/064; A61B 17/0642
USPC ............................................ 623/17.11–17.16
See application file for complete search history.

(56) References Cited

U.S. PATENT DOCUMENTS

| | | | |
|---|---|---|---|
| 3,791,380 A | 2/1974 | Dawidowski | |
| 3,875,595 A | 4/1975 | Froning | |
| 3,948,262 A | 4/1976 | Zaffaroni | |
| 4,349,921 A | 9/1982 | Kuntz | |
| 4,507,115 A | 3/1985 | Kambara et al. | |
| 4,599,086 A | 7/1986 | Doty | |
| 4,714,469 A | 12/1987 | Kenna | |
| 4,721,103 A | 1/1988 | Freedland | |
| 4,790,303 A | 12/1988 | Steffee | |
| 4,834,757 A | 5/1989 | Brantigan | |
| 5,263,953 A | 11/1993 | Bagby | |
| 5,300,074 A | 4/1994 | Frigg | |
| 5,401,269 A | 3/1995 | Buettner-Janz et al. | |
| 5,417,712 A * | 5/1995 | Whittaker | A61B 17/0401 606/232 |
| 5,458,638 A | 10/1995 | Kuslich et al. | |
| 5,522,845 A * | 6/1996 | Wenstrom, Jr. | A61B 17/0401 606/232 |
| 5,522,899 A | 6/1996 | Michelson | |
| 5,609,635 A | 3/1997 | Michelson | |
| 5,658,335 A | 8/1997 | Allen | |
| 5,683,394 A | 11/1997 | Rinner | |
| 5,800,547 A | 9/1998 | Schaefer et al. | |
| 5,800,550 A | 9/1998 | Sertich | |
| 5,810,820 A | 9/1998 | Santori et al. | |
| 5,849,004 A * | 12/1998 | Bramlet | A61B 17/0401 606/310 |
| 5,888,223 A | 3/1999 | Bray, Jr. | |
| 5,888,228 A | 3/1999 | Knothe et al. | |
| 5,889,905 A | 3/1999 | Leone | |
| 5,899,905 A | 5/1999 | Errico et al. | |
| 6,036,701 A | 3/2000 | Rosenman | |
| 6,113,638 A | 9/2000 | Williams et al. | |
| 6,120,503 A | 9/2000 | Michelson | |
| 6,136,001 A | 10/2000 | Michelson | |
| 6,139,550 A | 10/2000 | Michelson | |
| 6,179,873 B1 | 1/2001 | Zientek | |
| 6,193,721 B1 | 2/2001 | Michelson | |
| 6,210,442 B1 | 4/2001 | Wing et al. | |
| 6,214,050 B1 | 4/2001 | Huene | |
| 6,231,610 B1 | 5/2001 | Geisler | |
| 6,235,059 B1 | 5/2001 | Benezech et al. | |
| 6,258,089 B1 | 7/2001 | Campbell et al. | |
| 6,364,880 B1 | 4/2002 | Michelson | |
| 6,371,987 B1 | 4/2002 | Weiland et al. | |
| 6,383,186 B1 | 5/2002 | Michelson | |
| 6,398,783 B1 | 6/2002 | Michelson | |
| 6,413,259 B1 | 7/2002 | Lyons et al. | |
| 6,416,528 B1 | 7/2002 | Michelson | |
| 6,423,063 B1 | 7/2002 | Bonutti | |
| 6,428,542 B1 | 8/2002 | Michelson | |
| 6,432,106 B1 | 8/2002 | Fraser | |
| 6,447,546 B1 | 9/2002 | Bramlet et al. | |
| 6,454,771 B1 | 9/2002 | Michelson | |
| 6,468,309 B1 | 10/2002 | Lieberman | |
| 6,527,774 B2 | 3/2003 | Lieberman | |
| 6,527,776 B1 | 3/2003 | Michelson | |
| 6,527,803 B1 | 3/2003 | Crozet et al. | |
| 6,551,319 B2 | 4/2003 | Lieberman | |
| 6,558,423 B1 | 5/2003 | Michelson | |
| 6,592,586 B1 | 7/2003 | Michelson | |
| 6,616,666 B1 | 9/2003 | Michelson | |
| 6,620,163 B1 | 9/2003 | Michelson | |
| 6,626,907 B2 | 9/2003 | Campbell et al. | |
| 6,695,846 B2 | 2/2004 | Richelsoph et al. | |
| 6,712,818 B1 | 3/2004 | Michelson | |
| 6,746,450 B1 | 6/2004 | Wall et al. | |
| 6,767,367 B1 | 7/2004 | Michelson | |
| 6,770,096 B2 | 8/2004 | Bolger et al. | |
| 6,800,092 B1 | 10/2004 | Williams et al. | |
| 6,916,320 B2 | 7/2005 | Michelson | |
| 6,923,830 B2 | 8/2005 | Michelson | |
| 6,926,718 B1 | 8/2005 | Michelson | |
| 6,936,050 B2 | 8/2005 | Michelson | |
| 6,936,051 B2 | 8/2005 | Michelson | |
| 6,953,462 B2 | 10/2005 | Lieberman | |
| 6,969,390 B2 | 11/2005 | Michelson | |
| 6,981,975 B2 | 1/2006 | Michelson | |
| 7,037,340 B2 | 5/2006 | Gau | |
| 7,041,135 B2 | 5/2006 | Michelson | |
| 7,051,610 B2 | 5/2006 | Stoianovici et al. | |
| 7,056,344 B2 | 6/2006 | Huppert et al. | |
| 7,060,097 B2 * | 6/2006 | Fraser | A61F 2/442 623/17.13 |
| 7,074,221 B2 | 7/2006 | Michelson | |
| 7,077,844 B2 | 7/2006 | Michelson | |
| 7,112,206 B2 | 9/2006 | Michelson | |
| 7,137,984 B2 | 11/2006 | Michelson | |
| 7,172,627 B2 | 2/2007 | Fiere et al. | |
| 7,195,643 B2 | 3/2007 | Jackson | |
| 7,223,289 B2 | 5/2007 | Trieu et al. | |
| 7,255,698 B2 | 8/2007 | Michelson | |
| 7,290,972 B2 | 11/2007 | Gauthier | |
| 7,291,170 B2 | 11/2007 | Huppert | |
| 7,303,583 B1 | 12/2007 | Schaer et al. | |

(56) References Cited

U.S. PATENT DOCUMENTS

| | | |
|---|---|---|
| 7,326,250 B2 | 2/2008 | Beaurain et al. |
| 7,455,684 B2 | 11/2008 | Gradel et al. |
| 7,473,276 B2 | 1/2009 | Aebi et al. |
| 7,494,508 B2 | 2/2009 | Zeegers |
| 7,507,248 B2 | 3/2009 | Beaurain et al. |
| 7,563,284 B2 | 7/2009 | Coppes et al. |
| 7,563,286 B2 | 7/2009 | Gerber et al. |
| 7,594,931 B2 | 9/2009 | Louis et al. |
| 7,594,932 B2 | 9/2009 | Aferzon et al. |
| 7,625,381 B2 | 12/2009 | Michelson |
| 7,632,282 B2 | 12/2009 | Dinville |
| 7,637,950 B2 | 12/2009 | Baccelli et al. |
| 7,651,497 B2 | 1/2010 | Michelson |
| 7,662,182 B2 | 2/2010 | Zubok et al. |
| 7,662,185 B2 | 2/2010 | Alfaro et al. |
| 7,682,396 B2 | 3/2010 | Beaurain et al. |
| 7,695,516 B2 | 4/2010 | Zeegers |
| 7,695,518 B2 | 4/2010 | Gau |
| 7,704,255 B2 | 4/2010 | Michelson |
| 7,842,088 B2 | 11/2010 | Rashbaum et al. |
| 7,846,188 B2 | 12/2010 | Moskowitz et al. |
| 7,846,207 B2 | 12/2010 | Lechmann et al. |
| 8,002,835 B2 | 8/2011 | Zeegers |
| 8,075,618 B2 | 12/2011 | Trieu et al. |
| 8,080,062 B2 | 12/2011 | Armstrong et al. |
| 8,147,556 B2 | 4/2012 | Louis et al. |
| 8,162,988 B2 | 4/2012 | Delecrin et al. |
| 8,221,422 B2 | 7/2012 | Mangione |
| 8,221,457 B2 | 7/2012 | Delecrin et al. |
| 8,241,359 B2 | 8/2012 | Davis et al. |
| 8,257,439 B2 | 9/2012 | Zeegers |
| 8,257,443 B2 | 9/2012 | Kamran et al. |
| 8,262,700 B2 | 9/2012 | Cho et al. |
| 8,267,999 B2 | 9/2012 | Beaurain et al. |
| 8,303,663 B2 | 11/2012 | Jimenez et al. |
| 8,313,528 B1 | 11/2012 | Wensel |
| 8,323,345 B2 | 12/2012 | Sledge |
| 8,328,872 B2 | 12/2012 | Duffield et al. |
| 8,333,804 B1 | 12/2012 | Wensel |
| 8,343,197 B2 | 1/2013 | Gonzalez-Hernandez |
| 8,343,219 B2 | 1/2013 | Allain et al. |
| 8,353,219 B2 | 1/2013 | Brackett et al. |
| 8,409,288 B2 | 4/2013 | Davis et al. |
| 8,430,915 B2 | 4/2013 | Beaurain et al. |
| 8,439,931 B2 | 5/2013 | Dinville |
| 8,465,546 B2 | 6/2013 | Jodaitis et al. |
| 8,535,352 B2 | 9/2013 | Altarac et al. |
| 8,545,563 B2 | 10/2013 | Brun et al. |
| 8,617,245 B2 | 12/2013 | Brett |
| 8,641,766 B2 | 2/2014 | Donner et al. |
| 8,642,766 B2 | 2/2014 | Shenvi et al. |
| 9,044,337 B2 | 6/2015 | Dinville et al. |
| 9,408,715 B2 | 8/2016 | Donner et al. |
| 9,445,913 B2 | 9/2016 | Donner et al. |
| 9,539,110 B2 | 1/2017 | Bergey |
| 9,925,056 B2 | 3/2018 | Donner et al. |
| 2002/0004683 A1 | 1/2002 | Michelson |
| 2002/0059938 A1 | 5/2002 | Fogarty et al. |
| 2002/0082597 A1 | 6/2002 | Fraser |
| 2002/0099376 A1 | 7/2002 | Michelson |
| 2003/0028249 A1 | 2/2003 | Baccelli et al. |
| 2003/0149484 A1 | 8/2003 | Michelson |
| 2003/0187436 A1 | 10/2003 | Bolger et al. |
| 2003/0195514 A1 | 10/2003 | Trieu et al. |
| 2003/0195627 A1 | 10/2003 | Ralph et al. |
| 2004/0010312 A1 | 1/2004 | Enayati |
| 2004/0054411 A1 | 3/2004 | Kelly et al. |
| 2004/0068258 A1 | 4/2004 | Schlapfer et al. |
| 2004/0082953 A1 | 4/2004 | Petit |
| 2004/0093087 A1 | 5/2004 | Ferree et al. |
| 2004/0210219 A1 | 10/2004 | Bray |
| 2004/0220569 A1 | 11/2004 | Wall et al. |
| 2005/0027362 A1 | 2/2005 | Williams et al. |
| 2005/0049590 A1 | 3/2005 | Alleyne et al. |
| 2005/0101960 A1 | 5/2005 | Fiere et al. |
| 2005/0107788 A1 | 5/2005 | Beaurain et al. |
| 2005/0143825 A1 | 6/2005 | Enayati |
| 2005/0197706 A1 | 9/2005 | Hovorka et al. |
| 2005/0251258 A1 | 11/2005 | Jackson |
| 2005/0283236 A1 | 12/2005 | Razian |
| 2006/0022511 A1 | 2/2006 | Rompel |
| 2006/0030851 A1 | 2/2006 | Bray et al. |
| 2006/0085071 A1* | 4/2006 | Lechmann ............ A61F 2/4465 623/17.11 |
| 2006/0095071 A1 | 5/2006 | Zhang |
| 2006/0095136 A1 | 5/2006 | McLuen |
| 2006/0116676 A1 | 6/2006 | Gradel et al. |
| 2006/0241621 A1 | 10/2006 | Moskowitz et al. |
| 2006/0241764 A1 | 10/2006 | Michelson |
| 2006/0241778 A1 | 10/2006 | Ogilvie |
| 2006/0253201 A1 | 11/2006 | McLuen |
| 2006/0271053 A1 | 11/2006 | Schlapfer et al. |
| 2006/0276899 A1 | 12/2006 | Zipnick et al. |
| 2006/0282074 A1 | 12/2006 | Renaud et al. |
| 2007/0016295 A1 | 1/2007 | Boyd |
| 2007/0049943 A1 | 3/2007 | Moskowitz et al. |
| 2007/0073404 A1* | 3/2007 | Rashbaum ............ A61F 2/4425 623/17.14 |
| 2007/0106388 A1 | 5/2007 | Michelson |
| 2007/0162130 A1 | 7/2007 | Rashbaum et al. |
| 2007/0179623 A1 | 8/2007 | Trieu et al. |
| 2007/0208345 A1 | 9/2007 | Marnay et al. |
| 2007/0219635 A1 | 9/2007 | Mathieu et al. |
| 2007/0270960 A1 | 11/2007 | Bonin et al. |
| 2007/0270961 A1 | 11/2007 | Ferguson |
| 2008/0021562 A1 | 1/2008 | Huppert |
| 2008/0033432 A1 | 2/2008 | McGraw et al. |
| 2008/0132949 A1 | 6/2008 | Aferzon et al. |
| 2008/0177306 A1 | 7/2008 | Lamborne et al. |
| 2008/0234686 A1 | 9/2008 | Beaurain et al. |
| 2008/0249625 A1 | 10/2008 | Waugh et al. |
| 2008/0269768 A1 | 10/2008 | Schwager et al. |
| 2008/0281425 A1 | 11/2008 | Thalgott et al. |
| 2008/0306596 A1 | 12/2008 | Jones et al. |
| 2008/0312742 A1 | 12/2008 | Abernathie |
| 2008/0312743 A1 | 12/2008 | Vila et al. |
| 2009/0030520 A1 | 1/2009 | Biedermann et al. |
| 2009/0054988 A1 | 2/2009 | Hess |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0112271 A1 | 4/2009 | Moskowitz et al. |
| 2009/0118771 A1 | 5/2009 | Gonzalez-Hernandez |
| 2009/0149959 A1 | 6/2009 | Conner et al. |
| 2009/0164020 A1* | 6/2009 | Janowski ............ A61F 2/4465 606/247 |
| 2009/0210062 A1 | 8/2009 | Thalgott et al. |
| 2009/0210064 A1 | 8/2009 | Lechmann et al. |
| 2009/0216331 A1 | 8/2009 | Grotz et al. |
| 2009/0265007 A1 | 10/2009 | Colleran |
| 2010/0010547 A1 | 1/2010 | Beaurain et al. |
| 2010/0016974 A1 | 1/2010 | Janowski et al. |
| 2010/0049259 A1* | 2/2010 | Lambrecht ............ A61F 2/442 606/86 R |
| 2010/0050276 A1 | 2/2010 | Depaepe |
| 2010/0057206 A1 | 3/2010 | Duffield et al. |
| 2010/0145460 A1 | 6/2010 | McDonough et al. |
| 2010/0161057 A1 | 6/2010 | Berry et al. |
| 2010/0185289 A1* | 7/2010 | Kirwan .................. A61F 2/447 623/17.11 |
| 2010/0204796 A1* | 8/2010 | Bae ........................ A61F 2/447 623/17.16 |
| 2010/0234958 A1 | 9/2010 | Linares |
| 2010/0280618 A1 | 11/2010 | Jodaitis et al. |
| 2010/0298941 A1 | 11/2010 | Hes et al. |
| 2010/0305700 A1* | 12/2010 | Ben-Arye ............ A61B 17/70 606/279 |
| 2010/0305704 A1* | 12/2010 | Messerli ............ A61F 2/4455 623/17.16 |
| 2010/0312345 A1 | 12/2010 | Duffield et al. |
| 2010/0312346 A1 | 12/2010 | Kueenzi et al. |
| 2011/0054616 A1 | 3/2011 | Kamran et al. |

(56) References Cited

U.S. PATENT DOCUMENTS

| | | | |
|---|---|---|---|
| 2011/0077739 A1 | 3/2011 | Rashbaum et al. | |
| 2011/0098747 A1* | 4/2011 | Donner | A61B 17/7044 606/264 |
| 2011/0112587 A1 | 5/2011 | Patel et al. | |
| 2011/0166660 A1* | 7/2011 | Laurence | A61F 2/442 623/17.16 |
| 2011/0178599 A1 | 7/2011 | Brett | |
| 2011/0208311 A1 | 8/2011 | Janowski | |
| 2011/0230971 A1 | 9/2011 | Donner et al. | |
| 2012/0022654 A1 | 1/2012 | Farris et al. | |
| 2012/0053693 A1 | 3/2012 | Zeegers | |
| 2012/0078371 A1* | 3/2012 | Gamache | A61F 2/4465 623/17.16 |
| 2012/0078373 A1* | 3/2012 | Gamache | A61B 17/8052 623/17.16 |
| 2012/0116466 A1 | 5/2012 | Dinville et al. | |
| 2012/0191196 A1 | 7/2012 | Louis et al. | |
| 2012/0197404 A1 | 8/2012 | Brun et al. | |
| 2012/0265248 A1 | 10/2012 | Delecrin et al. | |
| 2012/0310356 A1 | 12/2012 | Davis et al. | |
| 2012/0330424 A1 | 12/2012 | Zeegers | |
| 2013/0013006 A1 | 1/2013 | Rashbaum et al. | |
| 2013/0041408 A1 | 2/2013 | Dinville et al. | |
| 2013/0150968 A1* | 6/2013 | Dinville | A61F 2/46 623/17.16 |
| 2013/0166029 A1 | 6/2013 | Dinville et al. | |
| 2013/0204300 A1 | 8/2013 | Michelson | |
| 2013/0226300 A1 | 8/2013 | Chataigner et al. | |
| 2013/0253648 A1 | 9/2013 | Beaurain et al. | |
| 2013/0253651 A1 | 9/2013 | Dinville | |
| 2013/0345814 A1* | 12/2013 | Walkenhorst | A61F 2/4465 623/17.16 |
| 2015/0025635 A1* | 1/2015 | Laubert | A61F 2/4611 29/428 |
| 2016/0081812 A1* | 3/2016 | Waugh | A61F 2/4455 623/17.16 |
| 2017/0014244 A1* | 1/2017 | Seifert | A61F 2/30771 |

FOREIGN PATENT DOCUMENTS

| | | |
|---|---|---|
| CA | 2445299 C | 1/2006 |
| CA | 2445303 C | 1/2006 |
| CA | 2445319 C | 1/2006 |
| CA | 2444232 C | 4/2006 |
| CA | 2444222 C | 5/2006 |
| CA | 2444226 C | 6/2006 |
| CA | 2523814 C | 2/2007 |
| CA | 2533689 C | 5/2007 |
| CA | 2533699 C | 5/2007 |
| CA | 2533695 C | 6/2007 |
| CA | 2533713 C | 6/2007 |
| CN | 1515234 A | 7/2004 |
| CN | 1620271 A | 5/2005 |
| CN | 101352367 A | 1/2009 |
| CN | 201244104 Y | 5/2009 |
| DE | 4327054 C1 | 4/1995 |
| EP | 0260044 A1 | 3/1988 |
| EP | 0667127 A1 | 8/1995 |
| EP | 1006913 B1 | 11/2005 |
| EP | 0891169 B1 | 12/2005 |
| EP | 1402836 | 7/2006 |
| EP | 1690508 A2 | 8/2006 |
| EP | 1393688 B1 | 4/2007 |
| EP | 1393689 B1 | 8/2007 |
| EP | 1847229 A2 | 10/2007 |
| EP | 1393687 B1 | 12/2007 |
| EP | 1402833 B1 | 5/2008 |
| EP | 2047825 A1 | 4/2009 |
| EP | 1402834 B1 | 1/2010 |
| EP | 1402832 B1 | 4/2011 |
| EP | 1402835 B1 | 9/2011 |
| EP | 2162098 B1 | 8/2015 |
| FR | 2727003 A1 | 5/1996 |
| FR | 2779941 A1 | 12/1999 |
| FR | 2848408 A1 | 6/2004 |
| FR | 2916956 A1 | 12/2008 |
| JP | 03-505416 A | 11/1991 |
| JP | 07-008514 A | 1/1995 |
| JP | 2796544 B2 | 9/1998 |
| JP | 11-506658 A | 6/1999 |
| JP | 2000-515041 A | 11/2000 |
| JP | 2001-187075 A | 7/2001 |
| JP | 2001-252283 A | 9/2001 |
| JP | 2002-518132 A | 6/2002 |
| JP | 2003-516174 A | 5/2003 |
| JP | 2004-500156 A | 1/2004 |
| JP | 2005-523074 A | 8/2005 |
| JP | 2006-510462 A | 3/2006 |
| JP | 2006-513752 A | 4/2006 |
| JP | 2006-230831 A | 9/2006 |
| JP | 2007-008514 A | 1/2007 |
| JP | 2007-090094 A | 4/2007 |
| JP | 2008-532730 A | 8/2008 |
| JP | 4167066 B2 | 10/2008 |
| JP | 2011-512893 A | 4/2011 |
| KR | 10-2010-0029755 A | 3/2010 |
| WO | 90/00037 A1 | 1/1990 |
| WO | 95/25469 A1 | 9/1995 |
| WO | 98/02105 A1 | 1/1998 |
| WO | 98/34553 A1 | 8/1998 |
| WO | 99/66867 A1 | 12/1999 |
| WO | 02/13732 A2 | 2/2002 |
| WO | 2002/058593 A2 | 8/2002 |
| WO | 2004/069106 A1 | 8/2004 |
| WO | 2004/080356 A2 | 9/2004 |
| WO | 2004/093767 A1 | 11/2004 |
| WO | 2005/092219 A1 | 10/2005 |
| WO | 2007/098288 A2 | 8/2007 |
| WO | 2007/127771 A2 | 11/2007 |
| WO | 2008/044057 A1 | 4/2008 |
| WO | 2008/102174 A2 | 8/2008 |
| WO | 2008/149223 A2 | 12/2008 |
| WO | 2009/004625 A2 | 1/2009 |
| WO | 2009/070721 A1 | 6/2009 |
| WO | 2009/131955 A1 | 10/2009 |
| WO | 2010/028045 A1 | 3/2010 |
| WO | 2010/121028 A2 | 10/2010 |
| WO | 2011/129973 A1 | 10/2011 |

OTHER PUBLICATIONS

International Patent Application No. PCT/US2011/029738: International Search Report dated Jun. 29, 2011, 12 pages.

Synthes, "Synthes Global Interent: SynFix-LR", http://www.Synthes.com/html/SynFix-LR.6902.0.html, Copyrights 2009, accessed Sep. 16, 2009, 1 page.

U.S. Provisional Application filed Apr. 15, 2009 by Lawton Laurence, et al., entitled "Arcuate Blade", U.S. Appl. No. 61/169,461.

U.S. Provisional Application filed Dec. 5, 2008 by Tom Overes,Langendorf, et al., entitled "Anchor-in-Anchor System for Use in Bone Fixation", U.S. Appl. No. 61/120,138.

* cited by examiner

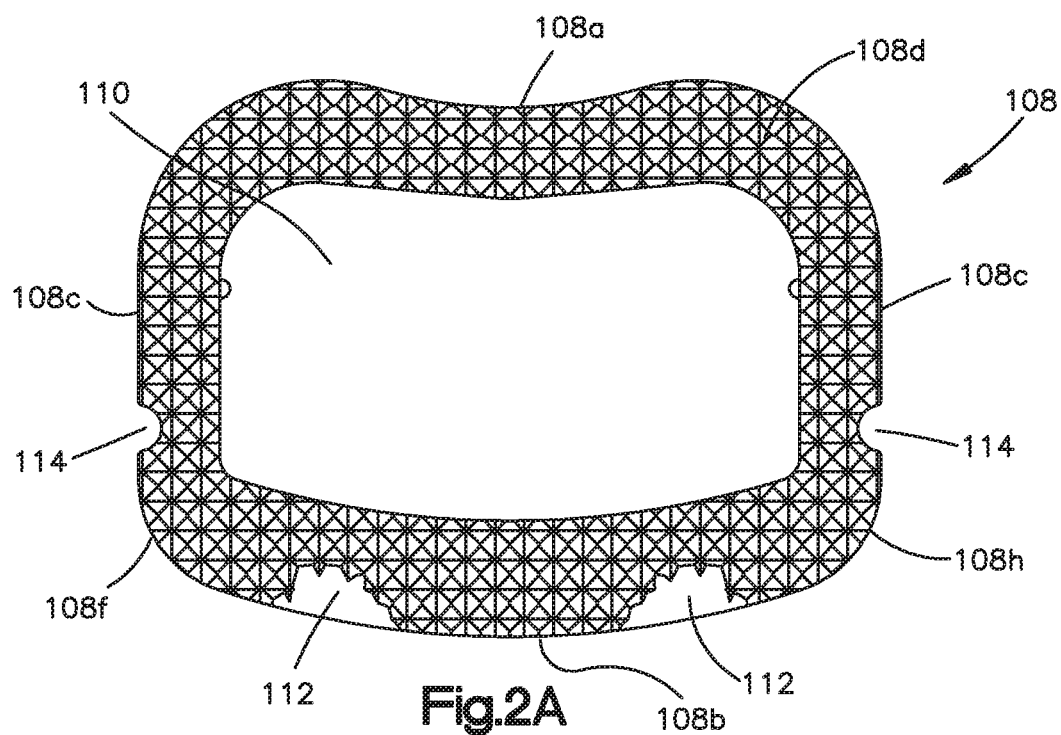
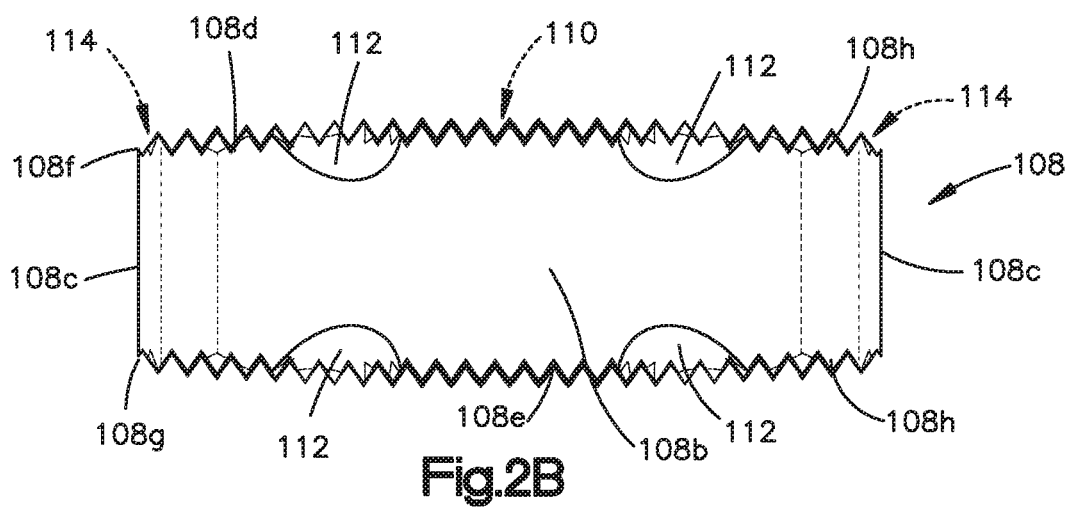
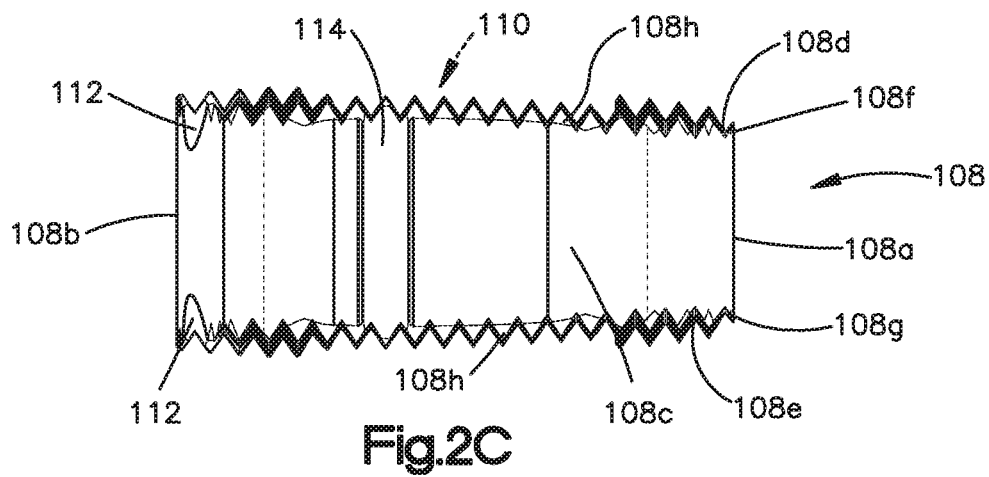

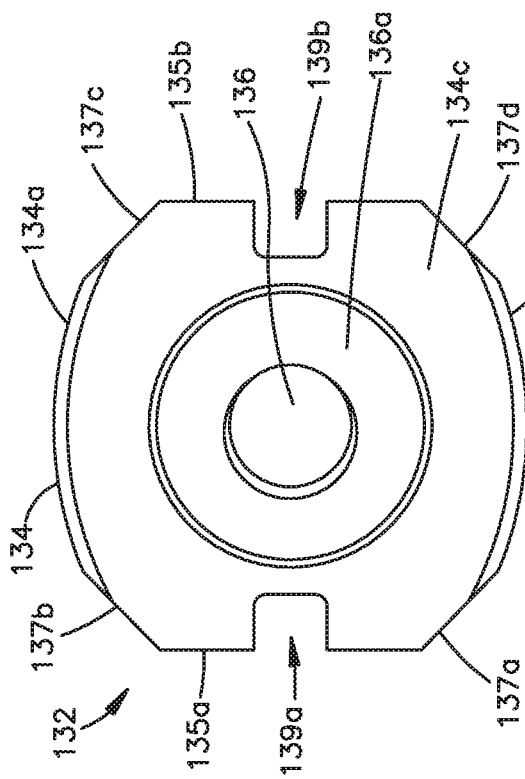
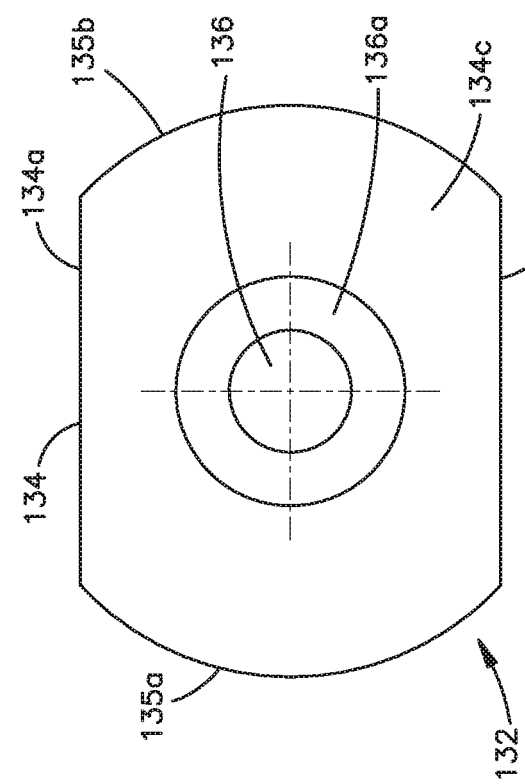
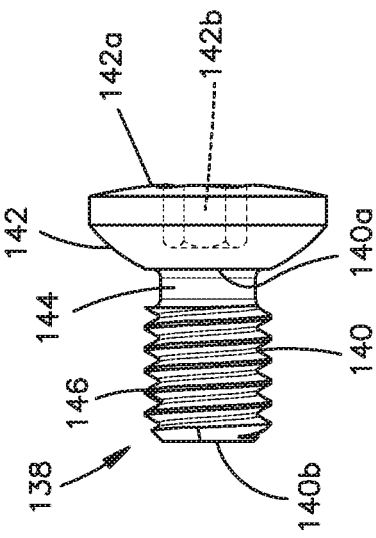
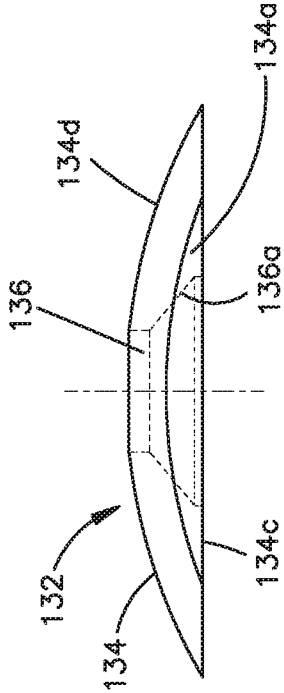

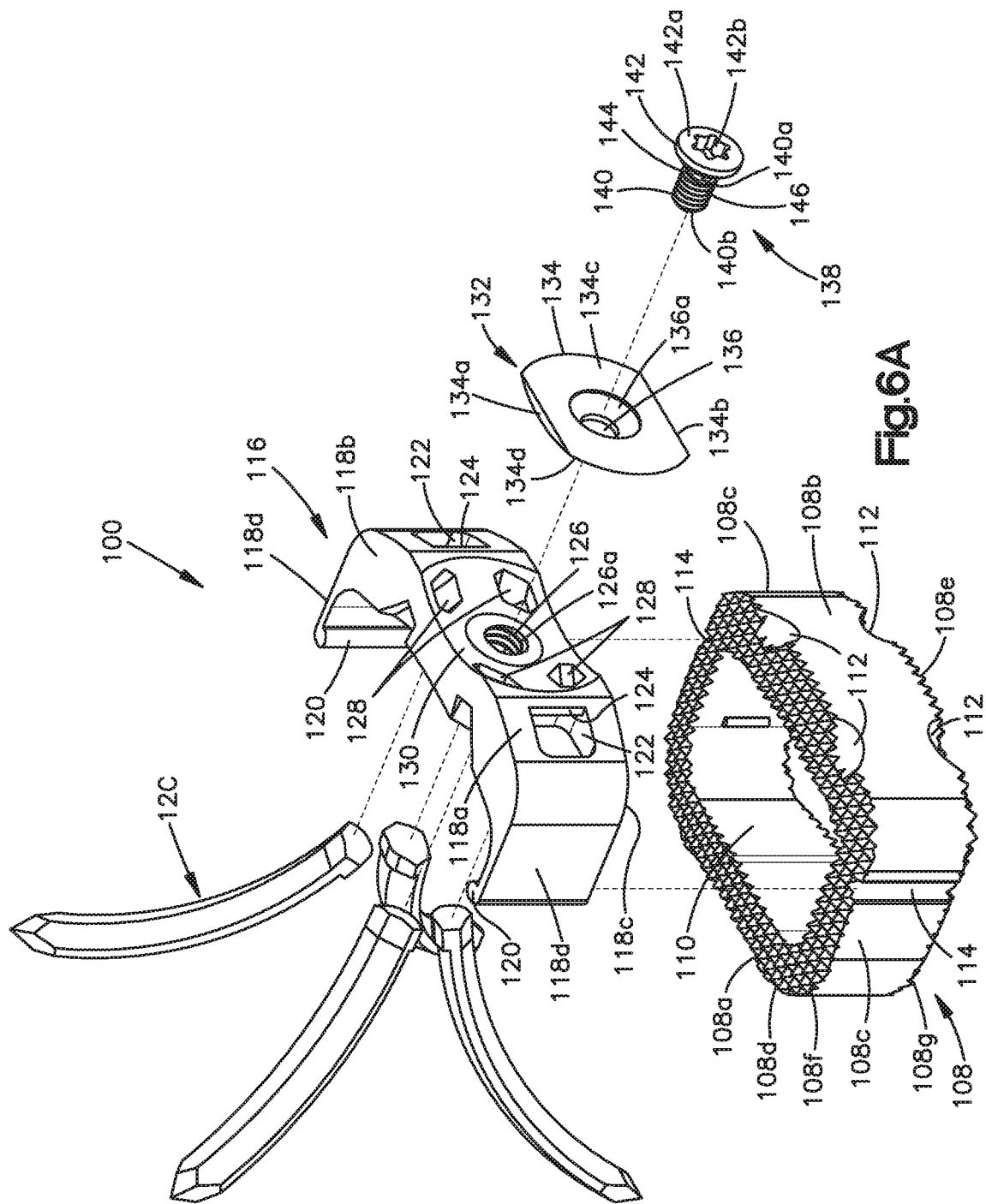

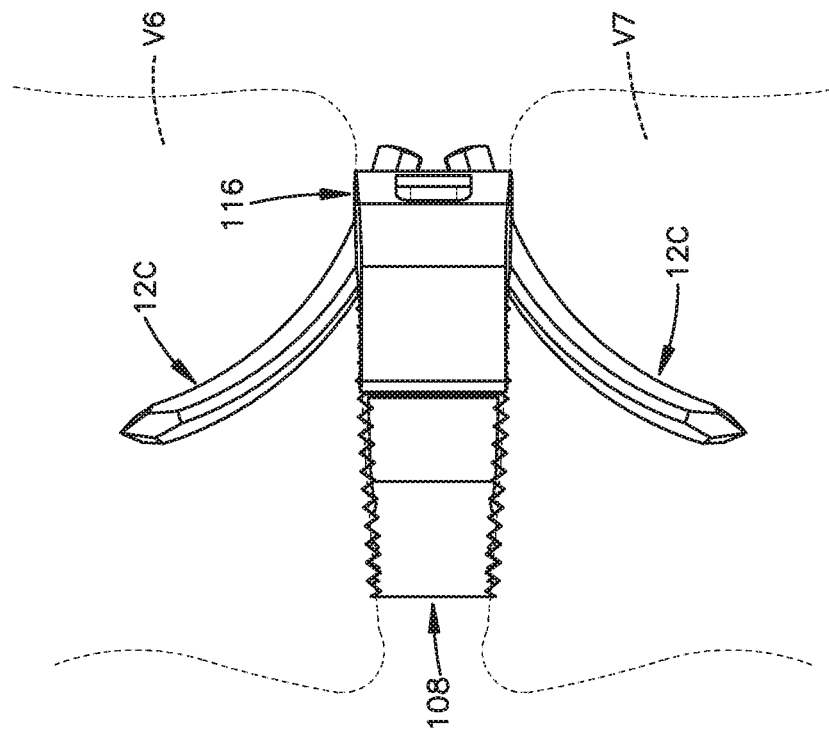
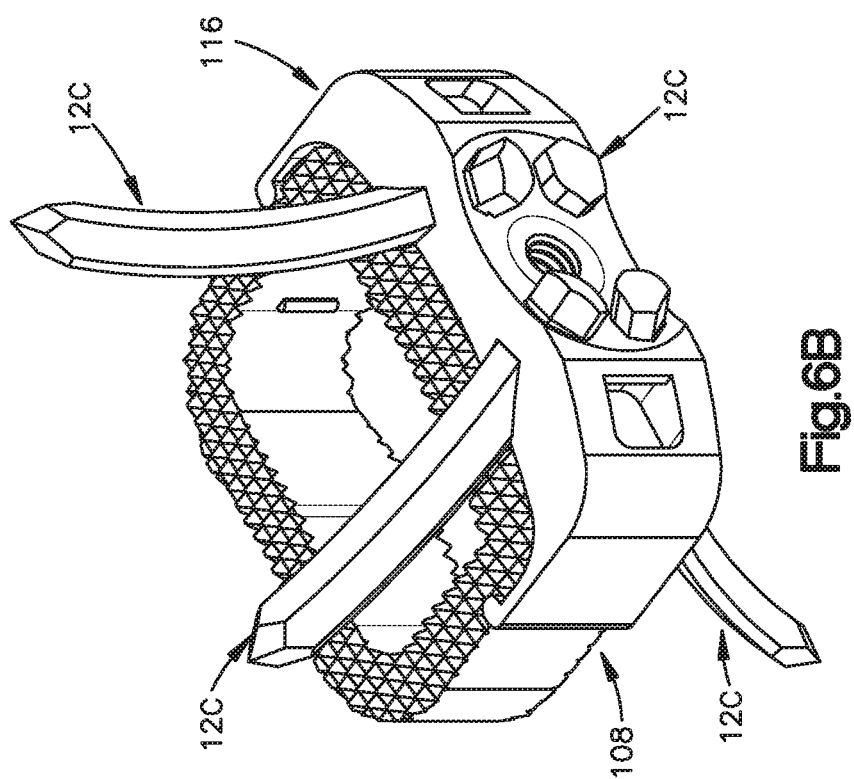

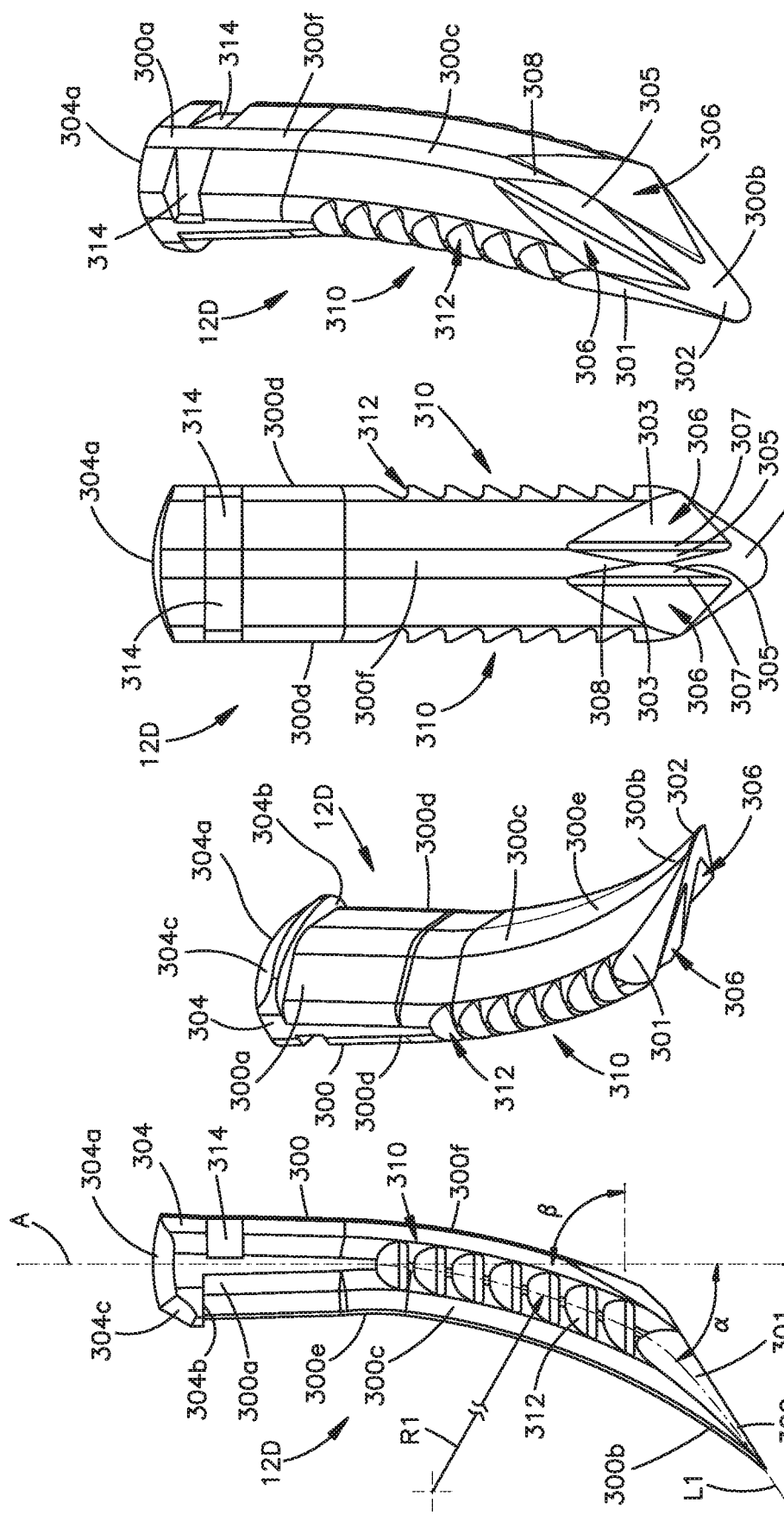

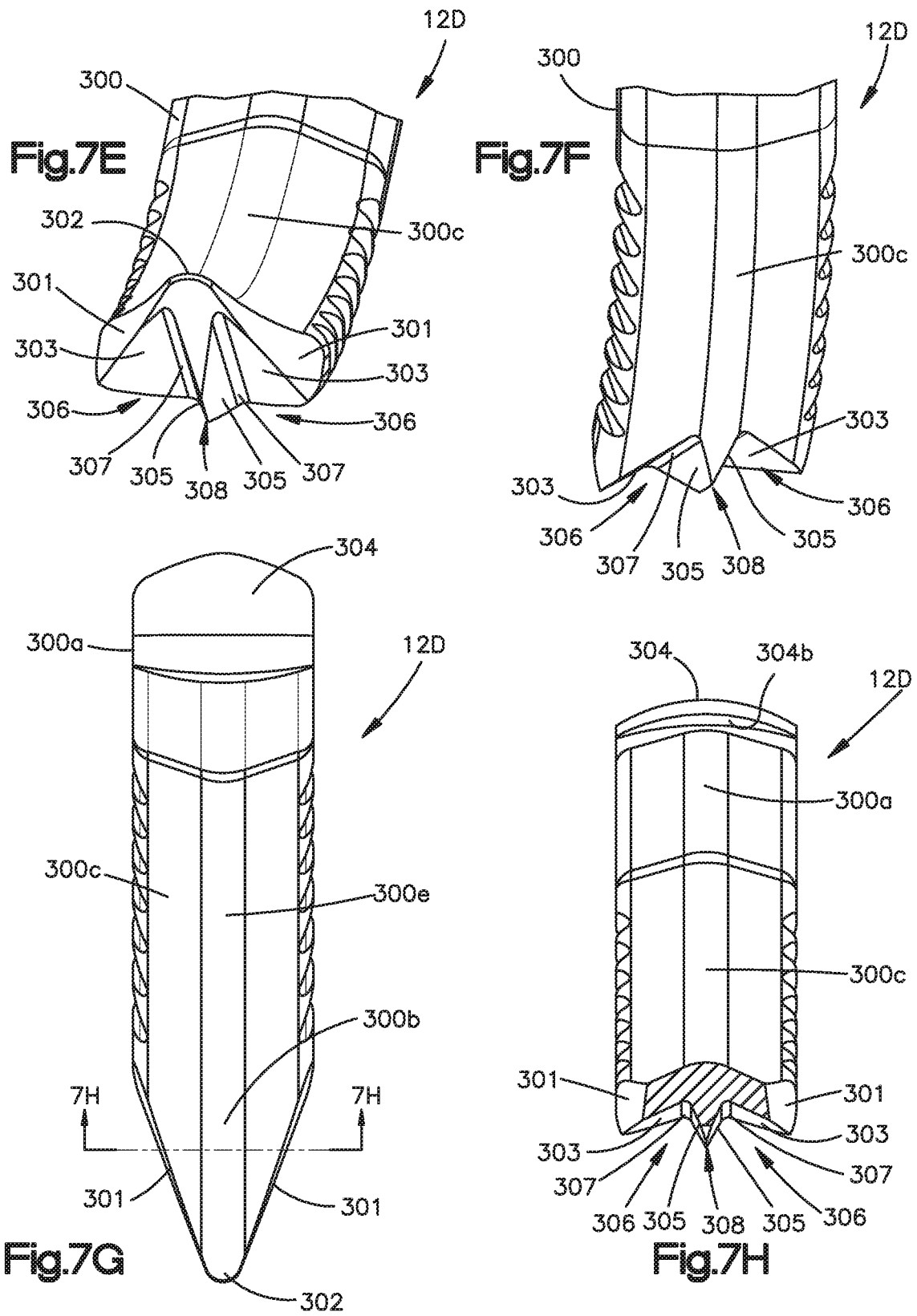

ARCUATE FIXATION MEMBER

CROSS-REFERENCE TO RELATED APPLICATIONS

This patent application is a continuation of U.S. patent application Ser. No. 15/898,991, filed Feb. 19, 2018, which is a continuation of U.S. patent application Ser. No. 15/060,566, filed Mar. 3, 2016, now U.S. Pat. No. 9,925,056, issued Mar. 27, 2018, which is a continuation of U.S. patent application Ser. No. 14/148,949, filed Jan. 7, 2014, now U.S. Pat. No. 9,445,913, issued Sep. 20, 2016, which is a continuation of U.S. patent application Ser. No. 13/070,883, filed Mar. 24, 2011, now U.S. Pat. No. 8,641,766, issued Feb. 4, 2014, which is a continuation-in-part of and claims priority to U.S. patent application Ser. No. 12/761,101, filed Apr. 15, 2010, now U.S. Pat. No. 9,408,715, issued Aug. 9, 2016, which claims priority to U.S. Provisional Patent Application No. 61/169,461, filed Apr. 15, 2009. The disclosures of each application listed in this paragraph are hereby incorporated by reference as if set forth in their entireties herein.

TECHNICAL FIELD

The present disclosure relates generally to orthopedics, and in particular relates to fixation systems, intervertebral implants, and associated surgical methods and procedures for using same.

BACKGROUND

Spinal fixation systems such as pedicle screw and rod constructs are commonly used to promote fusion between intervertebral bodies. The insertion of pedicle screws typically requires a linear "line-of-approach" trajectory that is aligned with the longitudinal axis of the screw, in order to accommodate the access and delivery instruments. Similarly, anchors such as bone screws may be used to directly fix intervertebral implants to vertebral bodies, typically requiring the insertion of several screws at unique angles oblique to the sagittal and/or transverse plane, and thus multiple lines-of-approach. However, in a variety of surgical situations, achieving a desired trajectory for screw insertion can be difficult due to the patient's anatomy obstructing a linear line-of-approach. For example, medially-directed placement of pedicle screws into the sacrum is desirable to prevent screw loosening and/or pullout, but can be prohibited due to the iliac crest obstructing the linear line-of-approach.

SUMMARY

In accordance with one embodiment, a bone fixation member configured to be inserted in a vertebral body includes a fixation body having opposing proximal and distal ends and a curved intermediate portion extending between the proximal and distal ends. A tip configured to cut into bone is defined at the distal end. A guidance member is disposed at the tip and extends toward the proximal end of the body. The guidance member is configured to guide the tip along an insertion trajectory as the fixation member is inserted into a vertebral body.

The bone fixation member can be used with an intervertebral implant that includes a spacer body that is configured to be implanted into an intervertebral space. The spacer body has an outer wall that defines at least a first aperture extending into the spacer body. The intervertebral implant also includes an insert that defines a plate. The insert is configured to be coupled to the spacer body such that the insert and the outer wall of the spacer body define a second aperture therebetween.

An alternative intervertebral implant that can be used with the bone fixation member includes a spacer body that has upper and lower plates and an outer wall extending between the upper and lower plates. The spacer body has a plurality of apertures extending through each of the upper and lower plates. The intervertebral implant also includes an insert that defines a plate. The insert is configured to be coupled to the spacer body such that the insert is disposed opposite at least a portion of the outer wall.

BRIEF DESCRIPTION OF THE DRAWINGS

The foregoing summary, as well as the following detailed description of the preferred embodiments of the application, will be better understood when read in conjunction with the appended drawings. For the purposes of illustrating the arcuate fixation member and intervertebral implants for use therewith, there are shown in the drawings preferred embodiments. It should be understood, however, that the instant application is not limited to the precise arrangements and/or instrumentalities illustrated in the drawings, in which:

FIG. 2A is a top elevation view of an intervertebral implant spacer for use with arcuate fixation members, constructed in accordance with an embodiment;

FIG. 2B is a front elevation view of the intervertebral implant spacer illustrated in FIG. 2A;

FIG. 2C is a side elevation view of the intervertebral implant spacer illustrated in FIG. 2A;

FIG. 4A is a front elevation view of a blocking plate for use with the insert plate illustrated in FIGS. 3A-B;

FIG. 4B is a top elevation view of the blocking plate illustrated in FIG. 4A;

FIG. 4C is a front elevation view of a blocking plate similar to the blocking plate illustrated in FIG. 4A, but constructed in accordance with an alternative embodiment;

FIG. 5 is a side elevation view of a locking screw for use with the insert plate and blocking plate illustrated in FIGS. 3A-B and 4A-B, respectively;

FIG. 6A is an exploded view of an intervertebral implant assembly constructed from the intervertebral implant system components illustrated in FIGS. 1A-5;

FIG. 6B is a perspective view of the intervertebral implant assembly illustrated in FIG. 6A, in an assembled configuration;

FIG. 6C is a side elevation view of the intervertebral implant assembly illustrated in FIG. 6B, inserted into an intervertebral space;

FIG. 7A is a side elevation view of an arcuate fixation member constructed in accordance with an alternative embodiment;

FIG. 7B is a front perspective view of the arcuate fixation member illustrated in FIG. 7A;

FIG. 7C is a rear elevation view of the arcuate fixation member illustrated in FIG. 7A;

FIG. 7D is a rear perspective view of the arcuate fixation member illustrated in FIG. 7A;

FIG. 7E is a front perspective view of a portion of the arcuate fixation member in FIG. 7A, showing a guidance member;

FIG. 7F is a rear perspective view of the portion of the arcuate fixation member in FIG. 7E;

FIG. 7G is a top elevation view of the arcuate fixation member illustrated in FIG. 7A;

FIG. 7H is a sectional front elevation view of the arcuate fixation member illustrated n FIG. 7G, taken along line 7H-7H;

DETAILED DESCRIPTION OF ILLUSTRATIVE EMBODIMENTS

Figure 1B:
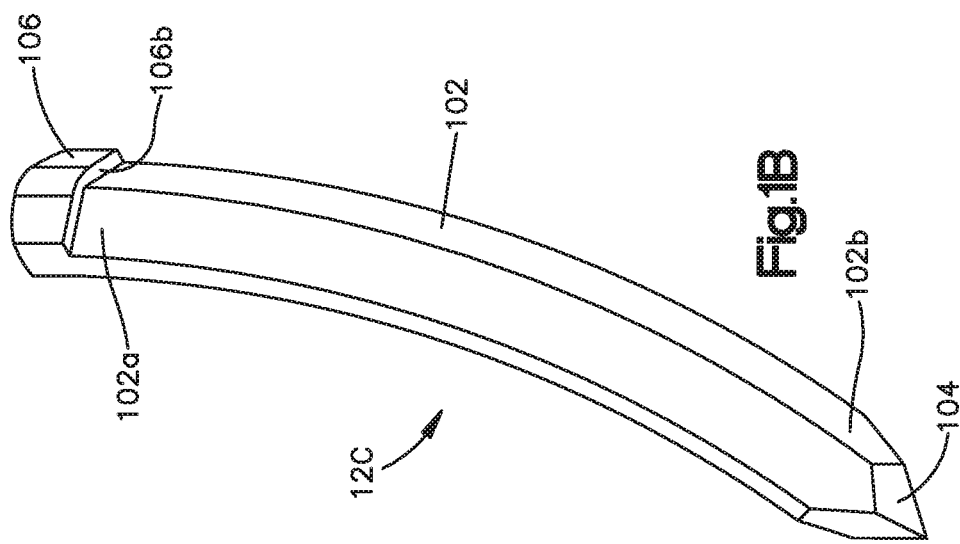
FIG. 1B is a perspective view of the arcuate fixation member illustrated in FIG. 1A.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior", "lateral", "medial", "sagittal", "axial", "coronal," "cranial," "caudal" and related words and/or phrases designate preferred positions and orientations in the human body to which reference is made and are not meant to be limiting.

The words "arcuate" and "curved" as used herein refer generally to the varying physical geometry of an object along an axis coincident to the object, for example the deviation from straightness of the body of an arcuate fixation member along a central longitudinal axis defined within the body of the object between its proximal and distal ends. Generally, with reference to a straight axis projected from a first end of such an object, as distance from the first end of the object increases along the central longitudinal axis of the object, distance between the central longitudinal axis of the object and the straight axis increases more or less continuously, so that the body of the object defined along its central longitudinal axis takes on a curved or arcuate shape. The resulting curvature of the central longitudinal axis may exhibit a constant or uniform radius with respect to a point in space defined remotely from the body of the object. Alternatively, a non-uniform or varying radius of curvature may be defined. The curvature of the body of the object defined by the longitudinal axis may also vary in direction with respect to a Cartesian coordinate system. The curvature may be uniformly distributed along the body of the object, for example between the proximal and distal ends of the object, or may be localized within one or more distinct segments of the body of the object. The curvature of the object may be significantly smooth and continuous along its central longitudinal axis, may be defined by a series of straight interconnected segments where each successive segment defines an increasing angle between the central longitudinal axis of the body of the object and the straight axis, or any combination thereof.

The words "vertebral body" as used herein should be interpreted broadly to include all the bones and bony structures found within and in the immediate proximity of the human spinal system, including but not limited to those found in the cervical region, the thoracic region, the lumbar region, and the sacral curve region.

The terminology intended to be non-limiting includes the above-listed words, derivatives thereof and words of similar import.

Referring initially to FIGS. 1A-6C, example embodiments of components of an intervertebral implant system 100 comprising a bone fixation member which can define an arcuate fixation member 12C as illustrated, an intervertebral implant spacer 108, an insert plate 116, a blocking plate 132, and a locking screw 138 are illustrated. Applications of the intervertebral implant system 100 could include, but are not limited to, fixation of the endplate components of a total disc replacement to vertebral bodies, direct fixation of an intervertebral implant to vertebral bodies, fixation into osteoporotic bone, and the like. The use of the systems and/or methods utilizing arcuate fixation members disclosed herein are particularly suitable when a linear line-of-approach for delivering a fixation member is undesirable. It should be noted that the physical characteristics of the arcuate fixation members disclosed herein may cause them to be alternately described as curved fixation members, arcuate or curved blades, arcuate or curved pins, arcuate or curved nails, or other terms of similar descriptive import.

As will become appreciated from the description below, one or more fixation members 12C may be utilized to securely anchor an assembled configuration of intervertebral implant system 100 within an intervertebral space between adjacent vertebral bodies. Unless otherwise indicated, the intervertebral implant system 100 and its components can be manufactured from any suitable biocompatible material known in the art including but not limited to titanium, titanium alloy such as TAN, commercially pure titanium, stainless steel, tantalum, polymers such as polyether ether ketone (PEEK), reinforced plastics, allograft bone, and the like.

Figure 1A:
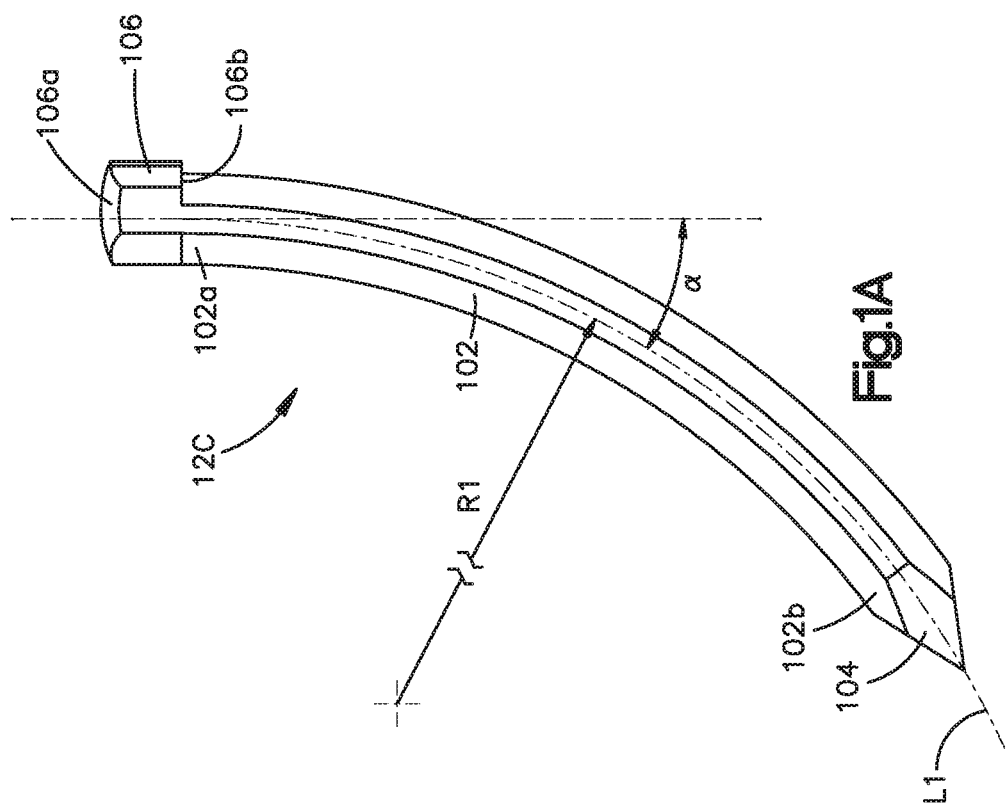
FIG. 1A is a side elevation view of an arcuate fixation member constructed in accordance with an embodiment.

Referring now to FIGS. 1A-B, the arcuate fixation member 12C includes a body 102 defining a proximal end 102a and a distal end 102b opposite the proximal end. The distal end 102b may comprise a tip 104 configured to cut into underlying structure or bone. The body 102 may further define an intermediate portion between the proximal end 102a and the distal end 102b that is curved along a central curved axis L1. In an embodiment, the intermediate portion is curved along substantially the entire length of the body 102 between the proximal end 102a and the distal end 102b. Alternatively, one or more distinct portions of the intermediate portion between the proximal end 102a and the distal end 102b may be curved (not shown).

In the illustrated embodiment, the intermediate portion is curved along the central curved axis L1 in accordance with a uniform radius of curvature R1. Alternatively, the intermediate portion may define a non-uniform radius of curvature along the central curved axis L1. In a preferred embodiment, the curvature of the intermediate portion may be smooth and continuous. Alternatively, the curvature of the intermediate portion may be defined by a series of substantially straight sections (not shown), with each substantially straight section aligned along an individual longitudinal axis corresponding to the individual section, where the magnitude of an angle α with respect to a perpendicular reference axis extended from the proximal end 102a increases in magnitude with the distance of each subsequent straight section from the proximal end 102a.

The arcuate fixation member 12C may have a head 106 defined at the proximal end 102a of the body 102. The head 106 may extend radially outward from the proximal end 102a of the body 102 in a direction perpendicular to the longitudinal axis L1. In an example embodiment, the head 106 may extend from the body 102 in a direction generally opposite from the direction of curvature of the body 102, as depicted in FIGS. 1A-B. In alternative embodiments, the head 106 may extend from the body 102 in a direction generally towards the direction of curvature of the body 102. The head may define an upper surface 106a configured for multi-angular engagement with a complementary surface of a delivery instrument, and a lower surface 106b opposite the upper surface 106a and configured to engage another component of the intervertebral implant system 100, for example the insert plate 116, when the arcuate fixation member 12C is in a fully inserted position.

Referring now to FIGS. 2A-C, the intervertebral implant spacer, or spacer 108 is defined by a posterior side 108a, an anterior side 108b opposite the posterior side, lateral sides 108c, an upper surface 108d, and a lower surface 108e opposite the upper surface. In an example embodiment, a portion of the posterior side 108a between the lateral sides 108c may be curved inwardly in the direction of the anterior side 108b, defining a rounded, generally rectangular kidney-like footprint, as depicted in FIG. 2A. In an alternative embodiment, a portion of the posterior side 108a between the lateral sides 108c may be curved outwardly in a direction away from the anterior side 108b (not shown). In another alternative embodiment, the posterior side 108a may be substantially straight between the lateral sides 108c, defining a rounded, generally rectangular footprint (not shown). The spacer 108 may have a central bore 110 defined therethrough, the shape of which substantially conforms to the footprint of the spacer 108 (e.g., a rounded, generally rectangular kidney-like footprint, or a rounded, generally rectangular footprint, depending upon the geometry of the posterior side 108a). The central bore 110 can be filled with bone growth inducing substances to allow bony ingrowth and to assist in fusion between the spacer 108 and adjacent vertebral bodies.

In an example embodiment of the spacer 108, the upper and lower surfaces 108d and 108e may have gripping structures 108h such as teeth, spikes, or similar structures, defined thereon and configured to facilitate gripping engagement between the upper and lower surfaces 108d and 108e and the end plates of adjacent vertebral bodies. The teeth 112 may be pyramidal, saw toothed or other similar shapes. In alternative embodiments of the spacer 108, portions of and/or the entirety of the upper and lower surfaces 108d and 108e may be substantially smooth and devoid of any protrusions. Upper and lower edges 108f and 108g, defined where the upper and lower surfaces 108d and 108e intersect with the posterior, anterior, and lateral sides 108a, 108b, and 108c respectively around the outer perimeter of the spacer 108, may be rounded (not shown). In an example embodiment, the upper and lower edges 108f and 108g may be rounded using a uniform radius of curvature around the perimeter of the implant. In an alternative embodiment, the upper and lower edges 108f and 108g may be rounded using a non-uniform radius of curvature around the perimeter of the implant. In another alternative embodiment, the upper and lower edges 108f and 108g along the anterior side 108b may be rounded with a greater radius than the remainder of the upper and lower edges 108f and 108g, such that a bull nose outer surface (not shown) is created on the anterior side 108b of the implant. Rounding upper and lower edges 108f and 108g may facilitate easier insertion of the spacer 108, for example by minimizing required distraction of the end plates of adjacent vertebral bodies.

In an example embodiment, the spacer 108 has a generally wedge-shaped side-view profile. As illustrated in FIG. 2C, this wedge shape is defined by a gradual decrease in the height of the spacer 108 (as measured between the upper and lower surfaces 108d and 108e) extending between the posterior side 108a in the direction of the anterior side 108b. The spacer 108 has a generally constant height between lateral sides 108c. In alternative embodiments, the spacer 108 may have a gradual increase in height followed by a gradual decrease in height extending from one lateral side 108c to the other, and/or may have a generally constant height between the posterior and anterior sides 108a and 108b, or may have convex and/or concave upper and lower surfaces 108d and 108e, thereby defining a gradual increase in height followed by a gradual decrease in height extending from the posterior side 108a to the anterior side 108b and from one lateral side 108c to the other.

A plurality of grooves 112 may be defined on the spacer 108 where the upper and lower surfaces 108d and 108e intersect with the anterior side 108b. The grooves 112 may be concave and may be configured to align with arcuate grooves 128 of the insert plate 116 when the spacer 108 and the insert plate 116 are in an assembled configuration. In an example embodiment, the grooves 112 may be substantially smooth and devoid of any protrusions. Retaining grooves 114 may be defined within the lateral sides 108c of the spacer 108 between the upper and lower surfaces 108d and 108e. The retaining grooves 114 may be configured to releasably engage complementary engaging ribs 120 of the insert plate 116.

Figure 3A:
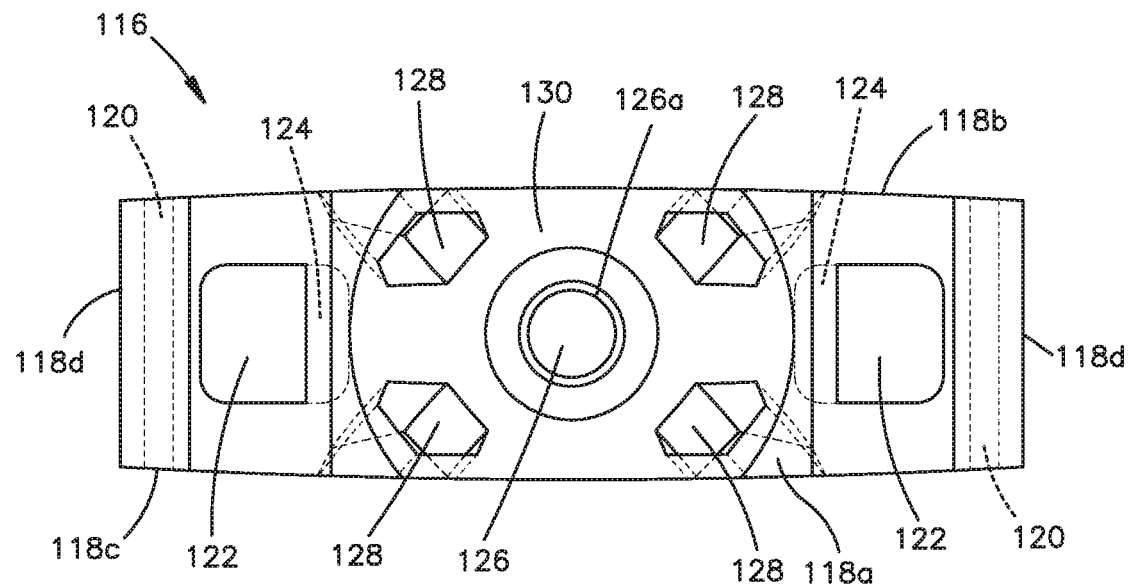
FIG. 3A is a front elevation view of an insert plate for use with the intervertebral implant spacer illustrated in FIGS. 2A-C.
Figure 3B:
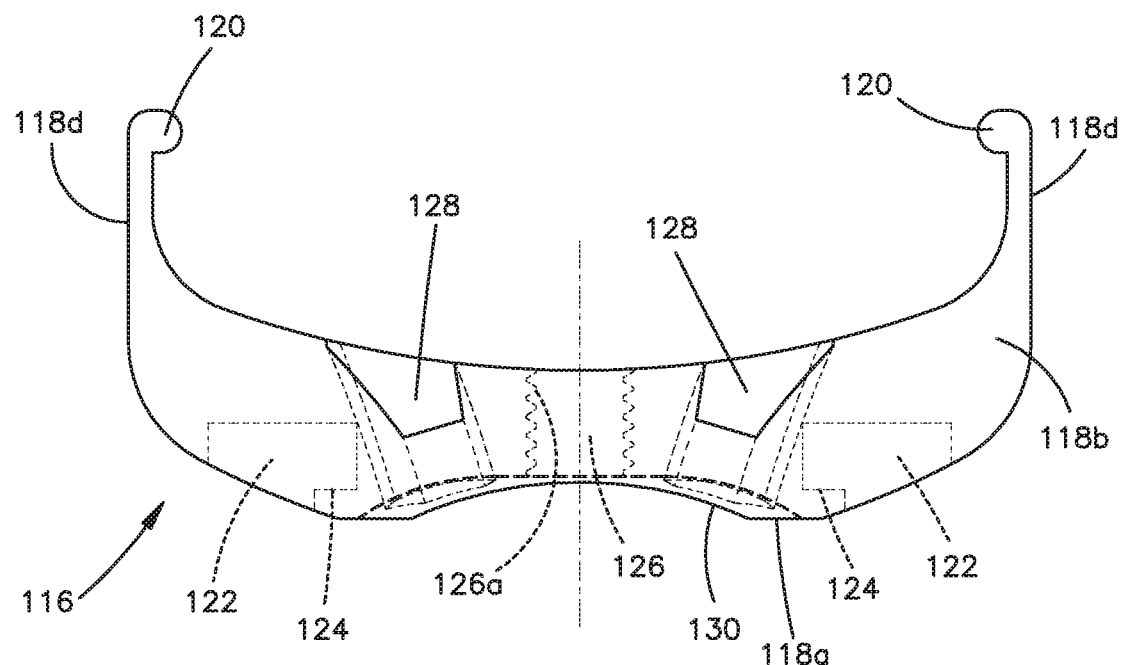
FIG. 3B is a top elevation view of the insert plate illustrated in FIG. 3A.
Figure 7J:
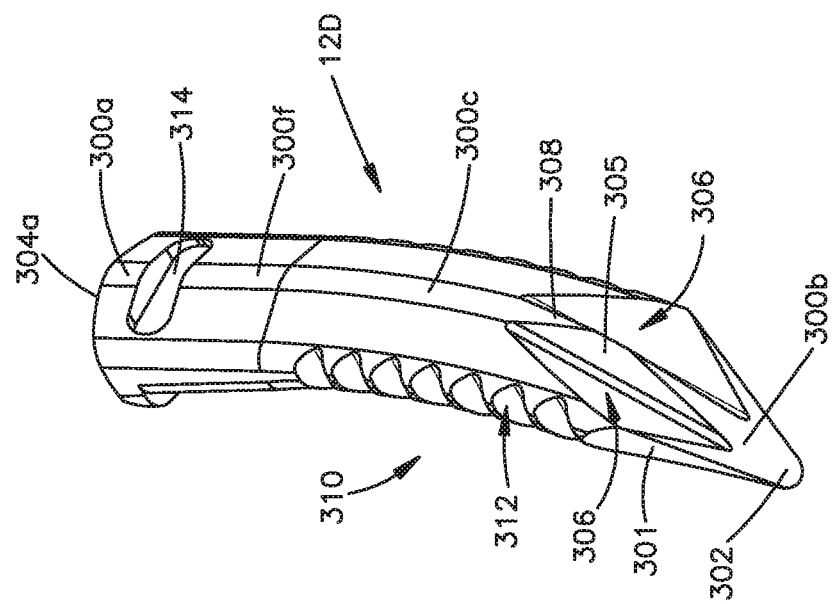
FIG. 7J is a rear perspective view of the arcuate fixation member illustrated in FIG. 7I.
Figure 7I:
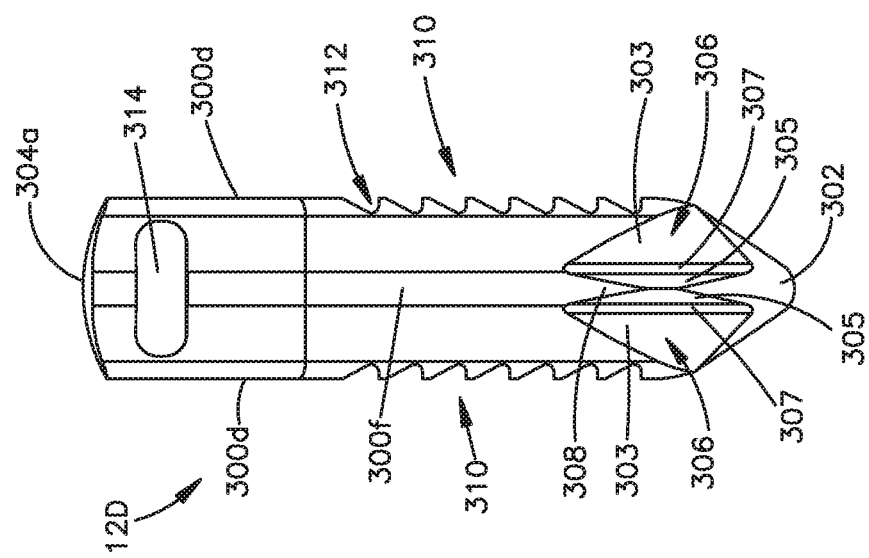
FIG. 7I is a rear elevation view of an arcuate fixation member similar to the arcuate fixation member illustrated in FIG. 7A, but constructed in accordance with an alternative embodiment.

Referring now to FIGS. 3A-B, the fixation plate, or insert plate, or insert 116 is defined by a generally C-shaped, channel-like body 118 that includes an anterior side 118a with upper and lower sides 118b and 118c opposite each other, and lateral sides 118d extending from opposite sides of the anterior side 118a in a generally perpendicular direction from the anterior side 118a. The anterior, upper, lower, and lateral sides 118a, 118b, 118c, and 118d may form a generally channel-like structure (in essence, a cradle) which may be configured to receive the anterior side 108b and at least a portion of the lateral sides 108c in partial nested engagement. As such, the upper and lower sides 108b and 108c may define gradual increases and/or decreases in height in a posterior direction from the anterior side 118a and/or between the lateral sides 108d, in order to generally conform the insert plate 116 to the geometry of the spacer 108. The lateral sides 118d may have engaging ribs 120 defined thereon at the ends opposite the anterior side 118a, the engaging ribs 120 configured to be releasably received within the retaining grooves 114 of the spacer 108.

The anterior side 118a of the insert plate 116 may have a pair of apertures 122 defined therethrough configured to receive grasping members of a delivery instrument. In an example embodiment, the apertures 122 may be D-shaped, as illustrated in FIG. 3A. However any other aperture shape may be defined as appropriate. The apertures 122 may have a retaining rib 124 defined therein configured to engage with a complementary grasping rib of the delivery instrument. The anterior side 118a of the insert plate 116 may also have a central bore 126 defined therethrough having an inner surface 126a with threads configured to engage complementary threads of a locking screw 138. The anterior side 118a of the insert plate 116 may also have a concave recess 130 defined therein configured to receive a complementary convex surface 134d of the blocking plate 132.

The anterior side 118a of the insert plate 116 may also have a plurality of arcuate grooves 128 defined therethrough configured to slidably receive the arcuate fixation members 12C and to define an insertion trajectory for each of the arcuate fixation members 12C. In an example embodiment, the arcuate grooves 128 may have a generally uniform cross sectional geometry configured to closely conform to the cross sectional geometry of the body 102 of the arcuate fixation member 12C between the head 106 and the distal end 102b. When an arcuate fixation member 12C is in a fully inserted position within a respective arcuate groove 128, the lower surface 106b of the head 106 will be engaged with the outer surface of the anterior side 118a of the insert plate 116. Because the upper surface 106a of the head 106 will not be flush with the outer surface of the anterior side 118a of the insert plate 116 in this configuration, it may be desirable to omit the blocking plate 132 and the locking screw 138. In an alternative embodiment, the arcuate grooves 128 have a recessed ledge defined therein in the area where the arcuate grooves 128 intersect with the outer surface of the anterior side 118a of the insert plate 116, the recessed ledge being configured to receive the lower surface 106b of the head 106 when the arcuate fixation member 12C is in a fully inserted position, such that the upper surface 106a of the head 106 is substantially flush with the outer surface of the anterior side 118a of the insert plate 116.

The arcuate grooves 128 may be disposed about the central bore 126 in any desired configuration and may define any insertion trajectories as appropriate. In the example embodiment depicted in FIGS. 3A-B, the arcuate grooves 128 are defined in opposing quadrants around the central bore 126, with two arcuate grooves 128 located near the upper side 118b and defining two generally cranial insertion trajectories, and two arcuate grooves 128 located near the lower side 118c and defining two generally caudal insertion trajectories. It should be noted that this configuration of arcuate groove 128 locations and arcuate fixation member 12C insertion trajectories is merely an example, and the scope of the instant disclosure should not be limited thereto.

Referring now to FIGS. 4A-B, the blocking plate 132 is defined by a generally disc-shaped body 134 with upper and lower surfaces 134a and 134b that can be planar as illustrated, an anterior surface 134c, and a posterior surface 134d. The disc-shaped body 134 can further define opposed side surfaces 135a and 135b, which can be convexly curved, extending between the upper and lower surfaces 134a-b. The upper and lower surfaces 134a and 134b and the height of the body 134 (as measured between the upper and lower surfaces 134a and 134b) may be defined to match the height (as measured between the upper and lower surfaces 118b and 118c) of the anterior side 118a of the insert plate 116 when the blocking plate 132 is in a fully assembled configuration. The anterior surface 134c of the body 134 may be generally planar, or may be defined to match the outer surface of the anterior side 118a of the insert plate 116 when the blocking plate 132 is in a fully assembled configuration. The posterior surface 134d may be defined as a convex surface configured to engage with the concave recess 130 of the insert plate 116 when the blocking plate 132 is in a fully assembled configuration.

The posterior surface 134d can also be configured to engage the heads 106 of the arcuate fixation members 12C inserted into the arcuate grooves 128 of the insert plate 116. For example, the posterior surface 134d can operate to drive the arcuate fixation members 12C into a fully inserted position within the insert plate 116 as the locking screw 138 is tightened. In addition to driving the arcuate fixation members 12C into a fully inserted position, the blocking plate 138 can additionally prevent backout of the arcuate fixation members 12C. It should be appreciated that the posterior surface 134d of the blocking plate 132 is not limited to the illustrated convex surface, and that the posterior surface 134d can define alternative geometries. For example, the posterior surface 134d may define a plurality of angled surfaces, such as four angled surfaces in opposed quadrants of the posterior surface 134d, each of the angled surfaces configured to engage with the head 106 of a corresponding arcuate fixation member 12C.

The body 134 may have an aperture 136 defined therethrough. In an example embodiment, the diameter of the aperture 136 may be slightly larger than the diameter of the central bore 126 of the insert plate 116, such that a locking screw 138 may be inserted into the aperture 136 with no interference therebetween. In another embodiment, the diameter of the aperture 136 may be substantially the same as that of the central bore 126, and the inner surface of the aperture 136 may have threads defined thereon, the threads configured to engage complementary threads of the locking screw 138. The aperture 136 may further be defined by a concave recess 136a defined within the anterior surface 134c, the concave recess 136a configured to receive the convex head 142 of the locking screw 138.

It should be appreciated that the blocking plate 132 can be geometrically configured as desired so as to be received and nest in the concave recess 362 and coupled to the insert plate 350. For instance, referring to FIG. 4C, the upper and lower surfaces 134a-b of the disc-shaped body 134 can be curved, and bow outwards in accordance with one embodiment. Furthermore, the side surfaces 135a-b can extend substantially straight between the upper and lower surfaces 134a-b. The disc-shaped body 134 can further define beveled surfaces 137a-d that are connected between respective side surfaces 135a and 135b and respective upper and lower surfaces 134a and 134b. Pockets 139 a-b can be defined extending into the side surfaces 135 a-b, the pockets 139a-b configured to receive a driving instrument that braces against the blocking plate 132 so as to drive the locking screw 138 into the insert plate 350.

Referring now to FIG. 5, the locking screw 138 includes a shaft 140 that defines longitudinally opposing proximal and distal ends 140a and 140b, respectively, and a head 142 coupled to the proximal end 140a of the shaft 140, either directly or indirectly via an unthreaded neck 144 that is coupled between the proximal end 140a of the shaft 140 and the head 142. The head 142 can define a generally convex shape between the interface of the head 142 and the neck 144 that extends outward towards a proximal end 142a of the head 142. The convex shape of the head may be configured to engage the concave recess 136a of the blocking plate 132. Of course, the head 142 can assume any other suitable alternative shape as appropriate. Helical threads 146 extend radially out from the shaft 140 at locations at and between the proximal and distal ends 140a and 140b that are configured to engage complementary threads on the inner surface 126a of the central bore 126 of the insert plate 116. Thus, a substantial entirety of the shaft 140 between the proximal and distal ends 140a and 140b may be threaded. The distal end 142a of the head 142 may have driving members 142b defined therein, designed to engage with complementary driving members of a delivery instrument. It should be appreciated that the locking screw 138 can alternatively be provided in combination with the blocking plate 132 as a captive locking screw, wherein the locking screw 138 is rotatably retained within the aperture 136 of the blocking plate 132. It should be appreciated that the head 142 can be externally threaded.

Referring now to FIGS. 6A-C, an example embodiment of the intervertebral implant system 100 is illustrated in an exploded view and in a nearly completely assembled configuration. FIG. 6B depicts the intervertebral implant system 100 partially assembled outside of an intervertebral space (the blocking plate 132 and locking screw 138 have been omitted for simplicity). The spacer 108 has been seated within the insert plate 116 such that the retaining ribs are seated with the retaining grooves 114 on the lateral sides of the spacer 108. Four arcuate fixation members 12C have been inserted through corresponding arcuate grooves 128 within the insert plate 116, and have been driven to an almost fully inserted position. In a final assembled configuration, the arcuate fixation members 12C would be driven into their fully inserted position, the blocking plate 132 would be received within the concave recess 130 in the anterior side of the insert plate 116, and the locking screw 138 would be driven into the central bore 126 of the insert plate 116 and finally tightened, thereby blocking the arcuate fixation members 12C from backing out of the assembled intervertebral implant system 100.

FIG. 6C depicts an example embodiment of the intervertebral implant system 100 partially assembled inside of an intervertebral space between adjacent vertebral bodies V6 and V7 (the blocking plate and locking screw have been omitted for simplicity). As an initial step, the spacer 108 has been prepared for insertion, for example by being packed a with bone growth inducing substance and or/having its outer surfaces properly prepared, and has been seated within the insert plate 116 such the retaining ribs are seated with the retaining grooves on the lateral sides of the spacer 108. The spacer 108 was then inserted into the intervertebral space between the adjacent vertebral bodies V6 and V7 using a delivery instrument (not shown). The delivery instrument was then used to deliver the four arcuate fixation members 12C into the arcuate grooves in the fixation plate 116 and drive them into an almost fully inserted position. During the final steps of the assembly process, the delivery instrument would be used to drive the arcuate fixation members 12C into their fully inserted position, the blocking plate would be received within the concave recess in the anterior side of the insert plate 116, and the locking screw would be driven into the central bore of the insert plate 116 and finally tightened, thereby blocking the arcuate fixation members 12C from backing out of the assembled intervertebral implant system 100.

Now referring generally to FIGS. 7A-14B, alternative example embodiments of components of the intervertebral implant system 100, for instance arcuate fixation member 12D, intervertebral implant spacers 316 and 336, and insert plate 350, are illustrated. Various embodiments of an intervertebral implant 400 can be constructed from the components of the intervertebral implant system 100, as described in more detail below. It should be noted preliminarily that in the interest of brevity, the figures and subsequent description pertaining to the arcuate fixation member 12D do not refer to certain features and/or uses of the arcuate fixation member 12C that may be integrated into the arcuate fixation member 12D, for example the use of the arcuate fixation member 12C in combination with above-described components of the intervertebral implant system 100, for instance the intervertebral implant spacer 108, the insert plate 116, the blocking plate 132, or the locking screw 138. However, embodiments in which those and other features of the arcuate fixation member 12C are integrated into the arcuate fixation member 12D are intended to be within the scope of the instant disclosure.

Referring now to FIGS. 7A-J, an alternative embodiment of the arcuate fixation member is illustrated. The arcuate fixation member 12D includes a fixation body, or body 300 defining a proximal end 300a, a distal end 300b opposite the proximal end, and an intermediate portion 300c extending between the proximal and distal ends 300a-b, respectively. The fixation body 300 has a cross sectional geometry that is substantially hexagonal, defining opposing laterally convex front and rear surfaces 300e-f extending between opposing sides, or edges 300d. The fixation body 300 defines a cross sectional geometry that is substantially constant throughout the intermediate portion 300c of the fixation body 300, and is tapered between lateral surfaces 301 converging along the edges 300d near the distal end 300b, defining a tip 302 configured to cut into an underlying structure, such as bone. The intermediate portion 300c of the fixation body 300 is curved along a central curved axis L1. It should be appreciated that the central curved axis L1 can define an insertion trajectory of the arcuate fixation member 12D into underlying structure, such as a vertebral body. It should be appreciated that the insertion trajectory can be differently defined, for example in accordance with alternative geometries of the arcuate fixation member 12D. In an embodiment, the intermediate portion 300c is curved along substantially the entire length of the fixation body 300 between the proximal and distal ends 300a-b, respectively. Alternatively, one or more distinct portions of the intermediate portion 300c can be curved (not shown).

In the illustrated embodiment, the intermediate portion 300c is curved along the central curved axis L1 in accordance with a uniform radius of curvature R1. Alternatively, the intermediate portion 300c can define a non-uniform radius of curvature along the central curved axis L1. In a preferred embodiment, the curvature of the intermediate portion 300c may be smooth and continuous. Alternatively, the curvature of the intermediate portion 300c can be defined by a series of substantially straight sections (not shown), with each substantially straight section aligned along an individual longitudinal axis corresponding to the respective individual section, where the magnitude of an angle α with respect to a perpendicular reference axis A extended from the proximal end 300a increases in magnitude with the distance of each subsequent straight section from the proximal end 300a. It should be appreciated that the cross sectional geometry of the fixation body 300 is not limited to the illustrated substantially hexagonal shape, and that the fixation body 300 can alternatively be defined with any suitable cross sectional geometry. It should further be appreciated that the cross sectional dimension of the fixation body 300 may vary, for example increasing or decreasing, throughout one or more portions of the intermediate portion 300c.

The arcuate fixation member 12D may have a head 304 defined at the proximal end 300a of the fixation body 300. The head 304 may extend radially outward from the proximal end 300a of the fixation body 300 in a direction perpendicular to the central curved axis L1. In an example embodiment, the head 304 may extend from the fixation body 300 in a direction generally towards the direction of curvature of the fixation body 300, as depicted in FIGS. 7A-D. In alternative embodiments, the head 304 may extend from the fixation body 300 in a direction generally opposite from the direction of curvature of the fixation body 300. The head 304 may define an upper surface 304a configured for multi-angular engagement with a complementary surface of a delivery instrument, and a lower surface 304b opposite the upper surface 304a and configured to engage another component of the intervertebral implant system 100, for example the insert plate 350, when the arcuate fixation member 12D is in an inserted position. The head 304 can have one or more tapered surfaces, for instance surface 304c, defined thereon, the tapered surface 304c configured to engage with a complementary surface in another component of the intervertebral implant system 100, for example the insert plate 350, thereby locking the arcuate fixation member 12D in an inserted position.

The fixation body 300 can define one or more guidance members, the guidance members configured to guide the tip 302 along an insertion trajectory as the arcuate fixation member 12D is inserted into an underlying structure, such as a vertebral body. In the illustrated embodiments, guidance members are disposed at distal end 300b of the fixation body 300, and in particular near the tip 302, but can alternatively be defined at any location on the fixation body 300. The fixation body 300 can define guidance members that are recessed within the fixation body 300, such as the illustrated flutes 306, or guidance members that comprise projections extending from the fixation body 300, such as the illustrated outer wings 303 and/or the keel 308, in any combination. For example, in the illustrated embodiment, a pair of recessed guidance flutes, or flutes 306 are defined by a keel 308 disposed between opposing wings 303.

The illustrated flutes 306 are defined by and are disposed at the tip 302 of the fixation body 300, the flutes 306 extending into the fixation body 300 from the tip 302 along directions substantially parallel to each other and to the insertion trajectory of the arcuate fixation member 12D, and terminating in the intermediate section 300c of the fixation body 300 proximal from the tip 302. In alternative embodiments, the flutes 306 can extend along directions that are angularly offset or otherwise non-parallel with respect to each other and/or with respect to the insertion trajectory. The flutes 306 are not limited to the illustrated length, and can alternatively be defined to terminate within the tip 302 of the fixation body, or to extend along any length, up to the entirety, of the fixation body 300. It should be appreciated that the flutes 306 can be symmetrically with respect to each other as illustrated, or asymmetrically. For example the flutes 306 can be defined with matching or different geometries, equal or different lengths, equal or different depths, etc.

The illustrated flutes 306 have a substantially "V" shaped geometry defined by outer wings, or wings 303 defined in the fixation body 300 and inner surfaces, or keel surfaces 305 defined in the fixation body 300, the wings 303 and keel surfaces 305 converging in troughs 307. The keel surfaces 305 define a keel 308, as described in more detail below, the flutes 306 are disposed between respective wings 303 and the keel 308. It should be appreciated that the wings 303 are not limited to the illustrated offset wings 303 disposed adjacent the keel 308 on respective sides of the keel 308, and that a single, up to a plurality of wings 303 can be defined at any location in the fixation body 300, for example substantially centrally between the edges 300d, offset laterally toward either edge 300d, or substantially along either edge 300d. It should further be appreciated that the wings 303 and/or the keel surfaces 305 are not limited to being defined within the cross sectional geometry of the fixation body 300, and can alternatively be defined to extend outwardly from the fixation body 300, for example from the front or rear surfaces 300e-f and/or the edges 300d. It should further still be appreciated that the geometries of the flutes 306 are not limited to the illustrated "V" shape, and can alternatively be defined with any suitable geometry.

The keel surfaces 305 define a projection from the fixation body 300, the projection configured as a guidance member in the form of a guidance keel, or keel 308. In the illustrated embodiment, the keel 308 is defined substantially centrally between the edges 300d of the fixation body 300, and disposed between the wings 303. In alternative embodiments, the keel 308 can be laterally offset toward either edge 300d. It should be appreciated that the arcuate fixation member 12D is not limited to a single keel 308 as illustrated, and that the fixation body 300 can define a plurality of keels 308 at any locations in the fixation body 300. It should further be appreciated that the arcuate fixation member 12D is not limited to the illustrated configuration of guidance members, and that the fixation body 300 can be differently constructed with any number of wings 303, flutes 306, keels 308, or any other guidance members, in any combination.

The fixation body 300 of the arcuate fixation member 12D can define one or more gripping structures configured to be retain the arcuate fixation member 12D in an inserted position within an underlying structure, such as a vertebral body. The gripping structures can include protrusions defined on the fixation body 300, such as teeth, spikes, or similar structures. For example, in the illustrated embodiment, a plurality of teeth 310 are defined in rows on opposing sides of the fixation body 300, in particular in the intermediate portion 300c of the fixation body 300 along the edges 300d. The illustrated plurality of teeth 310 are defined by a corresponding plurality of substantially "V" shaped notches 312 defined along the edges 300d of the fixation body 300. In the illustrated embodiment, the notches 312 are defined in parallel directions with respect to each other, such that the magnitude of an angle β between each notch 312 and the perpendicular reference axis A is maintained. In alternative embodiments, the notches 312 can be defined in directions that are not parallel with respect to each other, for example such that the magnitude of the angle β increases with the distance of each successive notch 312 from the proximal end 300a of the fixation body 300.

It should be appreciated that the gripping structures are not limited to being defined along the edges 300d of the fixation body 300, and that gripping structures supplemental to, or in lieu of, the illustrated teeth 310 can alternatively be defined in any other suitable location on the fixation body 300. It should further be appreciated that the gripping structures are not limited to the gripping structure geometry of the illustrated teeth 310, and that the fixation body 300 can alternatively define any other suitable gripping structure geometry. It should further still be appreciated that the number and/or geometry of the gripping structures can be defined so to add bone growth surface area to the arcuate fixation member 12D.

One or more removal members can be defined in the fixation body 300 of the arcuate fixation member 12D, the removal members allowing for distraction of the arcuate fixation member 12D from an underlying structure, such as a vertebral body. For example, in the embodiment illustrated in FIGS. 7A-H, a pair of grooves 314 are defined at the proximal end 300a of the fixation body 300, the grooves 314 extending into the fixation body 300 from the edges 300d. The illustrated grooves 314 are sized to receive complementary members of a removal tool. In an alternative embodiment illustrated in FIGS. 7I-J, a single groove 314 is defined at the proximal end 300a of the fixation body 300, the groove 314 extending into the rear surface 300f It should be appreciated that the arcuate fixation member 12D is not limited to the illustrated removal members, and that the fixation body 300 can be alternatively be defined with one or more other suitable removal members.

Referring now to FIGS. 8A-D, an alternative embodiment of the intervertebral implant spacer, or spacer is illustrated. The intervertebral implant spacer, or spacer 316 defines a spacer body, or body 318 configured to be implanted into an intervertebral space, the spacer body 318 having an outer wall 318c that defines an enclosed perimeter of the spacer body 318. In the illustrated embodiment, the outer wall 318c comprises an anterior wall 318a extending between opposing ends 318b, a posterior wall 318d opposite the anterior wall 318a, and opposing side walls 318e, the side walls 318e extending between the ends 318b of the anterior wall 318a and the posterior wall 318d. The spacer body 318 defines an upper surface 318f, and a lower surface 318g opposite the upper surface. The outer wall 318c defines an aperture 322 extending into the spacer body 318 through at least one of the upper or lower surfaces 318f-g.

Figure 8A:
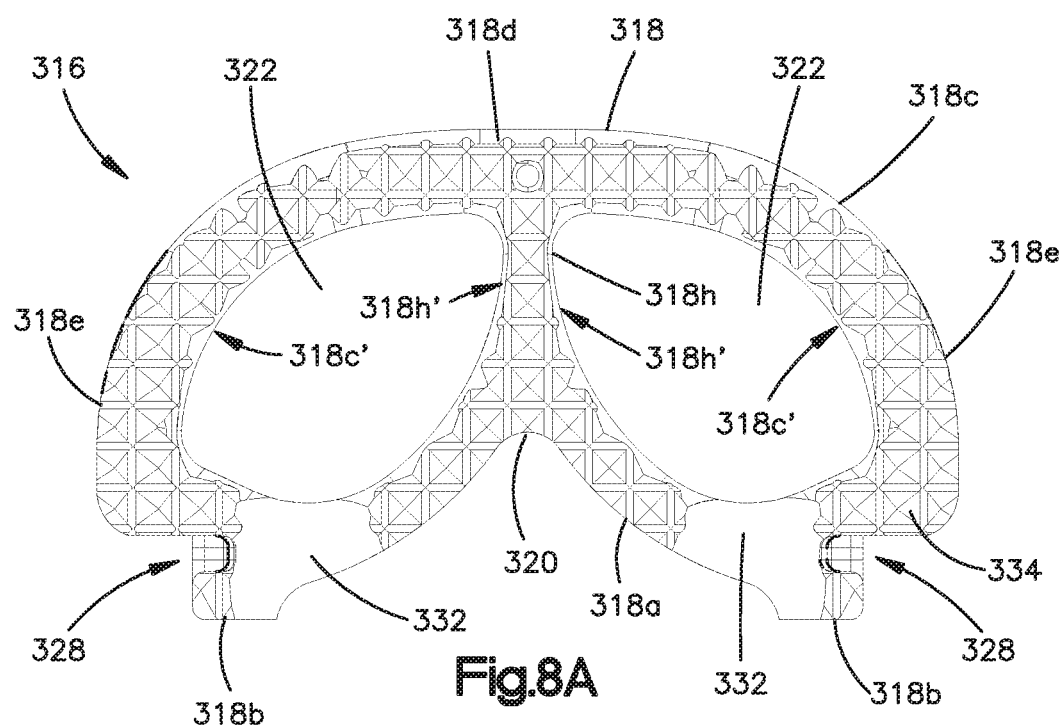
FIG. 8A is a top elevation view of an intervertebral implant spacer for use with arcuate fixation members, constructed in accordance with an alternative embodiment.
Figure 8B:
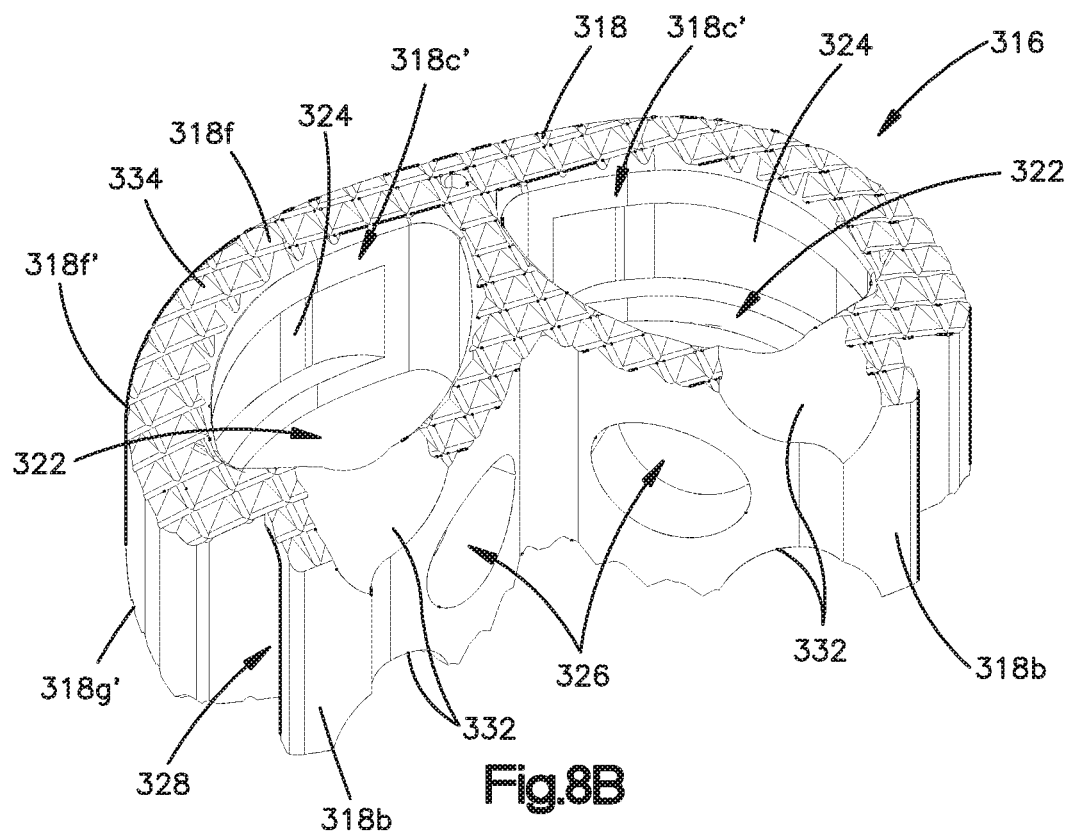
FIG. 8B is a perspective view of the intervertebral implant spacer illustrated in FIG. 8A.

A portion, up to an entirety of the anterior wall 318a can be curved inwardly toward the posterior wall 318d, defining an apex of curvature, or apex 320 in the anterior wall 318a approximately midway between the opposing ends 318b, as depicted in FIGS. 8A-B. Of course the apex 320 can be defined at any other location along the anterior wall 318a. In alternative embodiments, the anterior wall 318a can be straight between the ends 318b, can be curved outwardly away from the posterior wall 318d, or can define one or more distinct straight portions and/or curved portions between the ends 318b, thereby defining a corresponding number of apices 320 along the anterior wall 318a. It should be appreciated that the shape of the perimeter of the spacer body 318 is not limited to the illustrated geometry, and that the outer wall 318c can be differently constructed to define an alternatively shaped perimeter geometry of the spacer body 318.

The spacer body 318 can further include an inner wall 318h, the inner wall 318h defined so as to divide the aperture 322 defined by the outer wall 318c into a plurality of apertures 322. For example, in the illustrated embodiment, the inner wall 318h divides the aperture 322 defined by the outer wall 318c into a pair of apertures 322. The illustrated inner wall 318h extends between the apex 320 of the anterior wall 318a and the outer wall 318c, in particular between the apex 320 and substantially the midpoint of the posterior wall 318d. At least one additional aperture 322 can be defined between the anterior wall 318a and an insert plate, such as insert plate 350 (See FIGS. 10A-F) when the insert plate 350 is coupled to the spacer 316. One or more of the plurality of apertures 322 can be filled with bone growth inducing substances, for example to allow bony growth ingress and/or egress with respect to the spacer 316 and to assist in fusion between the spacer 316 and adjacent vertebral bodies.

In alternative embodiments, the spacer body 318 can be differently constructed, thereby alternatively defining the plurality of apertures 322. For example, it should be appreciated that the inner wall 318h can alternatively be defined to extend between any respective locations on the anterior wall 318a and the outer wall 318c. It should further be appreciated that the spacer body 318 is not limited to a single inner wall 318h as illustrated, and that alternatively a plurality of inner walls 318h having any combination of straight or curved geometries can be defined, the inner walls 318h of the plurality of inner walls 318h extending between a single or multiple locations on the anterior wall 318a and a single or multiple corresponding locations on the outer wall 318c, extending between respective locations on one or more inner walls 318h and the outer wall 318c, extending between a single or multiple locations on the outer wall 318c, extending from a single or multiple locations on the anterior wall 318a in a generally outward direction away from the posterior wall 318d, or any combination thereof. It should further still be appreciated that the respective thicknesses of the anterior wall 318a, the outer wall 318c, and/or the inner wall 318h can be uniform, or can have one or more portions of varying thickness.

One or more portions, up to an entirety of surfaces of the spacer body 318, for instance interior surfaces such as the inner surfaces 318c' of the outer wall 318c and/or the inner surfaces 318h' of the inner wall 318h, can be configured to allow bony ingrowth into the respective surfaces by bone growth inducing substances disposed into the apertures 322, for instance to enhance fusion between the spacer 316 and adjacent vertebral bodies and/or to provide a form of secondary fixation between an intervertebral implant 400 constructed with the spacer 316 and adjacent vertebral bodies. For example, one or more portions of the inner surface 318c' of the outer wall 318c can be recessed, defining respective cavities 324 therein. The cavities 324 can be open to respective apertures 322, such that the cavities 324 can be filled with bone growth inducing substances and/or to allow the above-described bony ingrowth into the cavities 324. It should be appreciated that the spacer body 318 is not limited to the illustrated cavities 324, and that the surfaces of the spacer body 318 can be differently constructed with any other geometries in order to allow body ingrowth.

The apertures 322 defined in the spacer body 318 can be configured to be in communication with each other, for example to facilitate biological communication between bone growth inducing substances in respective apertures 322 and/or to allow bony growth ingress and/or egress between the apertures 322. For example, one or more openings, such as openings 326 can be defined through the outer wall 318c and/or the inner wall 318h, the openings 326 placing two or more of the plurality of apertures 322 in communication with each other. In the illustrated embodiment, a pair of openings 326 are defined through the outer wall 318c, and in particular the anterior wall 318a. It should be appreciated that the spacer body 318 can alternatively configured to define one, up to a plurality of openings 326 through the outer wall 318c and/or the inner wall 318h at any locations along the outer wall 318c and/or the inner wall 318h.

The spacer 316 is configured to be coupled to an insert plate, such as insert plate 350. Coupling members can be defined on the spacer body 318, the coupling members configured to releasably mate with complementary coupling members of an insert plate. For example, in the illustrated embodiment, coupling members in the form of retaining grooves 328 are defined in the ends 318b of the anterior wall 318a, the retaining grooves 328 extending into the spacer body 318 from open ends 328a defined in the lower surface 318g and terminating in closed ends 328b near the upper surface 318f. The retaining grooves 328 are configured to receive complementary retaining members, such as the retaining members 356 defined on the insert plate 350, therein. The closed ends 328b of the retaining grooves 328 can operate to retain the retaining members 356 of an insert plate within the retaining grooves 328 and/or act as stops to ensure proper alignment between an insert plate and the spacer 316 during assembly. In an alternative embodiment, the spacer 316 can be constructed such that the retaining grooves 328 extend along the entirety of the body 318, such that both ends 328a-b are open.

Interlocking members can be defined on the coupling members, the interlocking members configured to be received in releasably locking engagement with complementary interlocking members defined on the retaining members 356 of the insert plate 350. For example, in the illustrated embodiment, interlocking members in the form of locking ridges 330 are defined in the retaining grooves 328, the locking ridges 330 sized to be received in releasably locking engagement within complementary locking grooves 358 defined on the retaining members 356 of the insert plate 350. In addition to locking the insert plate 350 into position with respect to the spacer 316, the interlocking members can be configured to facilitate a desired alignment in the transverse, or cranial-caudal direction between the insert plate and the spacer 316. For example, the illustrated locking ridges 330 are located within the retaining grooves 328 at a location approximately equal to the height wise midpoint of the anterior wall 318a, thereby ensuring that when the retaining members 356 are inserted into the retaining grooves 328 such that the locking ridges 330 are received in the locking grooves 358 (see FIG. 11B), the spacer 316 and the insert plate will achieve a desired transverse alignment with respect to each other.

The upper and lower surfaces 318f-g of the spacer body 318 can define a plurality of relief members, such as relief grooves 332, the relief grooves 332 configured to align with guide apertures 366 of the insert plate 350 (see FIGS. 10A-E) and to partially receive the fixation bodies 300 of respective arcuate fixation members 12D therein when an intervertebral implant 400 is assembled from the spacer 316 and an insert plate 350 and one or more arcuate fixation members 12D are inserted into the guide apertures 366 of the insert plate 350 and driven into position in an underlying structure, such as a vertebral body. In the illustrated embodiment, the relief grooves 332 are concave and are substantially smooth and devoid of any protrusions. It should be appreciated that the spacer 316 can be alternatively constructed without the relief grooves 332.

The upper and lower surfaces 318f-g of the spacer body 318 can be configured as bone-engaging surfaces, for example by defining gripping structures thereon, such as teeth, spikes, or the like. The gripping structures can be configured to engage adjacent underlying structures, such as the endplates of adjacent vertebral bodies, when the intervertebral implant 400 is inserted into an intervertebral space. In the illustrated embodiment, the upper and lower surfaces 318f-g have teeth 334 defined thereon. The teeth 334 may be pyramidal, saw toothed or other similar shapes. In alternative embodiments of the spacer 316, portions of, up to the entirety of the upper and/or lower surfaces 318f-g can be substantially smooth and devoid of any gripping structures.

The upper perimeter edge, or upper edge 318f and the lower perimeter edge, or lower edge 318g' of the spacer body 318, defined along the outer periphery of the spacer body 318 where the outer surface of the outer wall 318c intersects with the upper and lower surfaces 318f-g, respectively, can be rounded. Rounding the upper and lower edges 318f-g' can facilitate easier insertion and/or removal of the spacer 316, and thus the intervertebral implant 400, from an intervertebral space, for example by minimizing required distraction of the end plates of adjacent vertebral bodies. Distinct portions, up to an entirety of the upper and lower edges 318f-g' can be rounded using a varying radius of curvature. For example, in the illustrated embodiment respective portions of the upper and lower edges 318f-g' along the posterior wall 318d are rounded with a greater radius of curvature than the remainder of the upper and lower edges 318f-g', such that a "bullet tip" profile is defined on the posterior wall 318d of the spacer body 318, as depicted in FIG. 8D. In alternative embodiments, the upper and lower edges 318*f*-*g*' can be rounded using a substantially constant radius of curvature.

The upper and lower surfaces 318*f*-*g* can be defined as partially, up to fully convex surfaces. In the illustrated embodiment, the convexity of the upper and lower surfaces 318*f*-*g* in the anterior-posterior direction between the anterior wall 318*a* and the posterior wall 318*d* differs from the convexity of the upper and lower surfaces 318*f*-*g* in the lateral direction between the side walls 318*e*. The upper and lower surfaces 318*f*-*g* are fully convex in the anterior-posterior direction, and exhibit asymmetric convexity with respect to each other, wherein the anterior-posterior convexity of the upper surface 318*f* is defined using a shorter radius than the radius used to define the convexity of the lower surface 318*g*. In other words, the upper surface 318*f* exhibits a greater amount of curvature than the lower surface 318*g*. The upper and lower surfaces 318*f*-*g* are partially convex in the lateral direction, and exhibit symmetric convexity with respect to each other, wherein the lateral convexities of the upper and lower surfaces 318*f*-*g* are equal, or mirror images of each other. In particular, the upper and lower surfaces 318*f*-*g* define substantially no convexity in the lateral direction throughout the region C2, and are convex in the lateral direction in the regions C1 near the side walls 318*e*.

It should be appreciated that the geometry of the upper and lower surfaces 318*f*-*g* is not limited to the convexity of the illustrated embodiment, and that the upper and lower surfaces 318*f*-*g* can be defined with full or partial convexity in the anterior-posterior and/or lateral directions, with full or partial concavity in the anterior-posterior and/or lateral directions, with a combination of partial convexity and concavity in the anterior-posterior and/or lateral directions, or with no curvature at all (i.e., substantially flat) in the anterior-posterior and/or lateral directions. It should further be appreciated that the regions C1 and C2 can be defined with wider or narrower widths in the lateral direction. It should further still be appreciated that the geometry of the upper and lower surfaces 318*f*-*g* can be defined either symmetrically or asymmetrically with respect to each other.

Figure 8C:
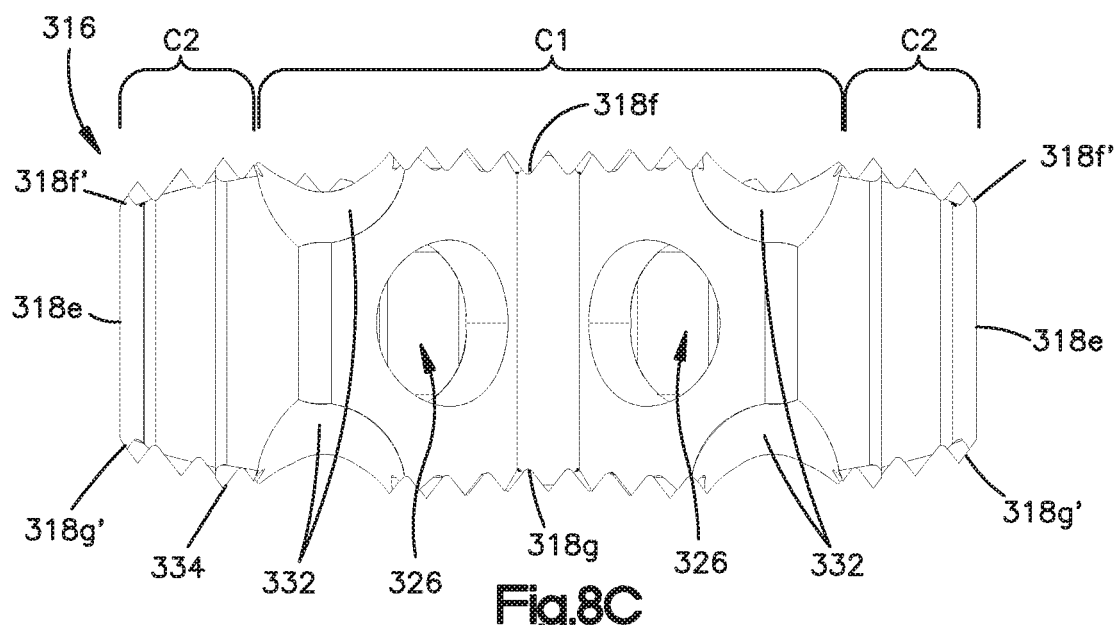
FIG. 8C is a front elevation view of the intervertebral implant spacer illustrated in FIG. 8A.
Figure 8D:
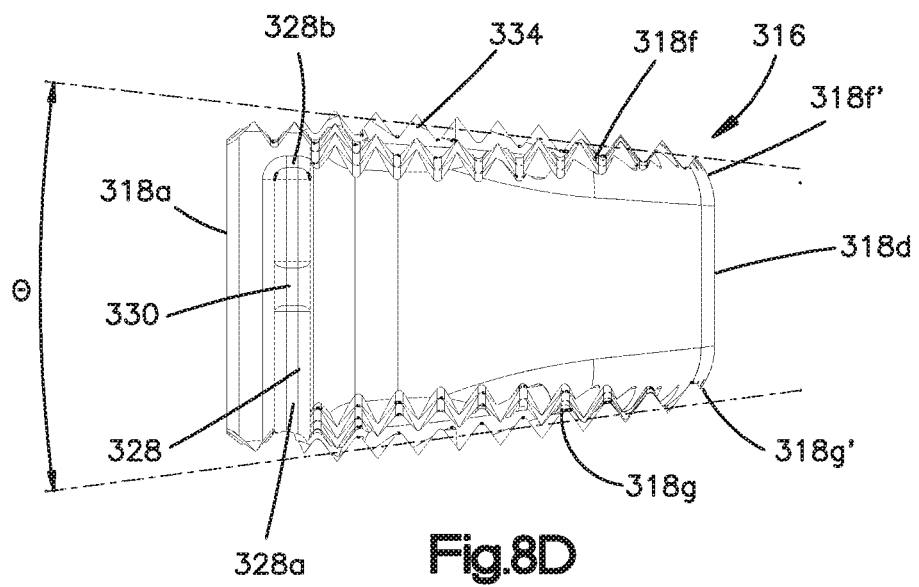
FIG. 8D is a side elevation view of the intervertebral implant spacer illustrated in FIG. 8A.

Referring now to FIGS. 8C-D, the illustrated embodiment of the spacer 316 has a generally wedge shaped side view profile defined by a gradual increase in height followed by a gradual decrease in height between the anterior wall 318*a* and the posterior wall 318*d*, and a generally rectangular front view profile defined by a generally constant height throughout the C2 region, and gradually decreasing height throughout the C1 regions between the opposing ends of the C2 region and the side walls 318*e*. In alternative embodiments the height between the anterior wall 318*a* and the posterior wall 318*d* of the spacer 316 may gradually decrease, may gradually increase, may have a gradual decrease followed by a gradual increase, or may be generally constant, while the height between the side walls 318*e* may increase and/or decrease, or may be generally constant.

The geometry of the spacer 316, for instance the geometry of the upper and lower surfaces 318*f*-*g* and/or the difference in the height of the body 318 between the anterior and posterior walls 318*a*, 318*d* defines a lordotic angle θ of the spacer 316. The lordotic angle θ defined by the spacer 316 can be increased and/or decreased by varying the geometry of the spacer 316. For example, the lordotic angle θ defined by the illustrated spacer 316 can be increased by heightening the anterior wall 318*a* of the spacer 316 while maintaining the height of the posterior wall 318*d*. In preferred embodiments, the anterior-posterior convexity defined by the upper surface 318*f* is increased with increasing magnitude of the lordotic angle θ, while the anterior-posterior convexity defined by the lower surface 318*g* is maintained. It should be appreciated that when the geometry of the spacer 316 is alternatively constructed in order to increase or decrease the lordotic angle θ defined by the spacer 316, the anterior-posterior convexity and/or the lateral convexity of the upper and/or lower surfaces 318*f*-*g* can be increased or decreased in any combination such that the upper and lower surfaces 318*f*-*g* are defined the same or differently.

Referring now to FIGS. 9A-D, another alternative embodiment of the intervertebral implant spacer, or spacer is illustrated. The intervertebral implant spacer, or spacer 336 defines a generally hollow spacer body, or body 338 having an open anterior end 338*a* defined between opposing ends 338*b*, an outer wall 338*c* extending around a perimeter of the spacer body 336 between the ends 338*b*, and opposing upper and lower plates 338*f*-*g*, the outer wall 338*c* extending between the upper and lower plates 338*f*-*g*. The upper and lower plates 338*f*-*g* define respective upper and lower surfaces 338*h*-*i*. In the illustrated embodiment, the outer wall 338*c* is defined by a posterior wall 338*d* opposite the anterior end 338*a* and opposing side walls 338*e*, the side walls 338*e* extending between the ends 338*b* and the posterior wall 338*d*. It should be appreciated that the shape of the perimeter of the spacer body 338 is not limited to the illustrated geometry, and that the outer wall 338*c* can be differently constructed to define an alternatively shaped perimeter geometry of the spacer body 338.

The spacer body 338 can have a plurality of openings, such as apertures 340 and/or slots 342 defined therethrough, for example to allow bony growth ingress and/or egress with respect to the spacer body 338, the bony growth ingress and/or egress assisting in fusion between the spacer 336 and adjacent vertebral bodies and/or providing a form of secondary fixation between an intervertebral implant 400 constructed with the spacer 336 and adjacent vertebral bodies. In the illustrated embodiment, a plurality of apertures 340 are defined extending through the upper and lower plates 338*f*-*g*, and a plurality of slots 342 are defined extending through the outer wall 338*c*. The apertures 340 that extend through each of the respective plates can have varying diameters with respect to each other and extend through the plates at locations that define a pattern that can be repeated between the upper and lower plates 338*f*-*g* such that the each of the apertures 340 that extend through the upper plate 338*f* are aligned with corresponding apertures that extend through the lower plate 338*g* with respect to central axes defined between respective apertures in a substantially transverse direction to the spacer body 338. The slots 342 are equally sized and elongate in the transverse direction between the upper and lower plates 338*f*-*g*, and are spaced equally from each other along the outer wall 338*c*.

The generally hollow interior of the spacer body 338 can be filled with bone growth inducing substances, for example to allow bony growth ingress and/or egress with respect to the spacer body 338 as described above. It should be appreciated that spacer body 338 is not limited to the illustrated apertures 340, that the upper and lower plates 338*f*-*g* can alternatively be defined with any number of apertures 340 of varying diameters and/or locations, and that the apertures 340 on the upper and lower plates 338*f*-*g*, respectively, can be defined the same or differently. It should further be appreciated that the spacer body 338 is not limited to the illustrated slots 342, that the outer wall 338*c* can alternatively be defined with any number of slots 342 of varying shapes and/or sizes, and that the slots 342 can be spaced apart from each other equally or differently. It should further still be appreciated that the openings defined in the spacer body 338 are not limited to the illustrated apertures 340 and slots 342, and that openings having any other geometry can be defined through the spacer body 338 at any respective locations, in addition to or in lieu of the apertures 340 and slots 342. It should further still be appreciated that the respective thicknesses of the upper plate 338, the lower plate 338g and/or the outer wall 338c can be uniform or can have one or more portions of varying thickness.

The spacer 336 is configured to be coupled to an insert plate, such as insert plate 350, such that the open anterior end 338a is disposed between the posterior end 338d and the insert plate. Coupling members can be defined on the spacer body 338 of the spacer 336, the coupling members configured to releasably mate with complementary coupling members of an insert plate. For example, in the illustrated embodiment, coupling members in the form of retaining grooves 344 are defined in the ends 338b of the anterior end 338a, the retaining grooves 344 extending into the spacer body 338 from open ends 344a defined in the lower surface 338i and terminating in closed ends 344b near the upper surface 338h. The retaining grooves 344 are configured to receive complementary retaining members, such as the retaining members 356 defined on insert plate 350, therein. The closed ends 344b of the retaining grooves 344 can operate to retain the retaining members 356 of an insert plate within the retaining grooves 344 and/or act as stops to ensure proper alignment between an insert plate and the spacer 336 during assembly. In an alternative embodiment, the spacer 336 can be constructed such that the retaining grooves 344 extend along the entirety of the body 338, such that both ends 344a-b are open.

Interlocking members can be defined on the coupling members, the interlocking members configured to be received in releasably locking engagement with complementary interlocking members defined on the retaining members 356 of the insert plate 350. For example, in the illustrated embodiment, interlocking members in the form of locking ridges 346 are defined in the retaining grooves 344, the locking ridges 346 sized to be received in releasably locking engagement within complementary locking grooves 358 defined on the retaining members 356 of the insert plate 350. In addition to locking the insert plate 350 into position with respect to the spacer 336, the interlocking members can be configured to facilitate a desired alignment in the transverse, or cranial-caudal direction between the insert plate and the spacer 336. For example, the illustrated locking ridges 346 are located within the retaining grooves 344 at a location approximately equal to the height wise midpoint of the anterior end 338a, thereby ensuring that when the retaining members 356 are inserted into the retaining grooves 344 such that the locking ridges 346 are received in the locking grooves 358 (see FIG. 11B), the spacer 336 and the insert plate will achieve a desired transverse alignment with respect to each other.

The upper and lower plates 338f-g of the spacer body 338 can define a plurality of relief members, such as relief grooves 339, the relief grooves 339 configured to align with guide apertures 366 of the insert plate 350 (see FIGS. 10A-E) and to partially receive the fixation bodies 300 of respective arcuate fixation members 12D therein when an intervertebral implant 400 is assembled from the spacer 336 and an insert plate 350 and one or more arcuate fixation members 12D are inserted into the guide apertures 366 of the insert plate 350 and driven into position in an underlying structure, such as a vertebral body. In the illustrated embodiment, the relief grooves 339 define edges 339a in the upper and lower surfaces 338h-i that are substantially smooth and devoid of any protrusions. It should be appreciated that the spacer 336 can be alternatively constructed without the relief grooves 339.

The upper and lower surfaces 338h-i of the spacer body 338 can be configured as bone-engaging surfaces, for example by defining gripping structures thereon, such as teeth, spikes, or the like. The gripping structures can be configured to engage adjacent underlying structures, such as the endplates of adjacent vertebral bodies, when the intervertebral implant 400 is inserted into an intervertebral space. In the illustrated embodiment, the upper and lower surfaces 338h-i have teeth 348 defined thereon. The teeth 348 may be pyramidal, saw toothed or other similar shapes. In alternative embodiments of the spacer 336, portions of, up to the entirety of the upper and/or lower surfaces 338h-i can be substantially smooth and devoid of any gripping structures.

The upper perimeter edge, or upper edge 338h' and the lower perimeter edge, or lower edge 338i' of the spacer body 338, defined along the outer periphery of the spacer body 338 where the outer surface of the outer wall 338c intersects with the upper and lower surfaces 338h-i, respectively, can be rounded. Rounding the upper and lower edges 338h'-i' can facilitate easier insertion and/or removal of the spacer 336, and thus the intervertebral implant 400, from an intervertebral space, for example by minimizing required distraction of the end plates of adjacent vertebral bodies. Distinct portions, up to an entirety of the upper and lower edges 338h'-i' can be rounded using a varying radius of curvature. For example, in the illustrated embodiment respective portions of the upper and lower edges 338h'-i' along the posterior wall 338d are rounded with a greater radius of curvature than the remainder of the upper and lower edges 338h'-i', such that a "bullet tip" profile is defined on the posterior wall 338d of the spacer body 338, as depicted in FIG. 9D. In alternative embodiments, the upper and lower edges 338h'-i' can be rounded using a substantially constant radius of curvature.

The upper and lower surfaces 338h-i can be defined as partially, up to fully convex surfaces. In the illustrated embodiment, the convexity of the upper and lower surfaces 338h-i in the anterior-posterior direction between the anterior end 338a and the posterior wall 338d differs from the convexity of the upper and lower surfaces 338h-i in the lateral direction between the side walls 338e. The upper and lower surfaces 338h-i are fully convex in the anterior-posterior direction, and exhibit asymmetric convexity with respect to each other, wherein the anterior-posterior convexity of the upper surface 338h is defined using a shorter radius that the radius used to define the convexity of the lower surface 338i. In other words, the upper surface 338h exhibits a greater amount of curvature than the lower surface 338i. The upper and lower surfaces 338h-i are partially convex in the lateral direction, and exhibit symmetric convexity with respect to each other, wherein the lateral convexity of the upper and lower surfaces 338h-i are equal, or mirror images of each other. In particular, the upper and lower surfaces 338h-i define substantially no convexity in the lateral direction throughout the region C4, and are convex in the lateral direction in the regions C3 near the side walls 338e.

It should be appreciated that the geometry of the upper and lower surfaces 338h-i is not limited to the convexity of the illustrated embodiment, and that the upper and lower surfaces 338h-i can be defined with full or partial convexity in the anterior-posterior and/or lateral directions, with full or partial concavity in the anterior-posterior and/or lateral directions, with a combination of partial convexity and concavity in the anterior-posterior and/or lateral directions, or with no curvature at all (i.e., substantially flat) in the anterior-posterior and/or lateral directions. It should further be appreciated that the regions C3 and C4 can be defined with wider or narrower widths in the lateral direction. It should further still be appreciated that the geometry of the upper and lower surfaces 338h-i can be defined either symmetrically or asymmetrically with respect to each other.

Figure 9A:
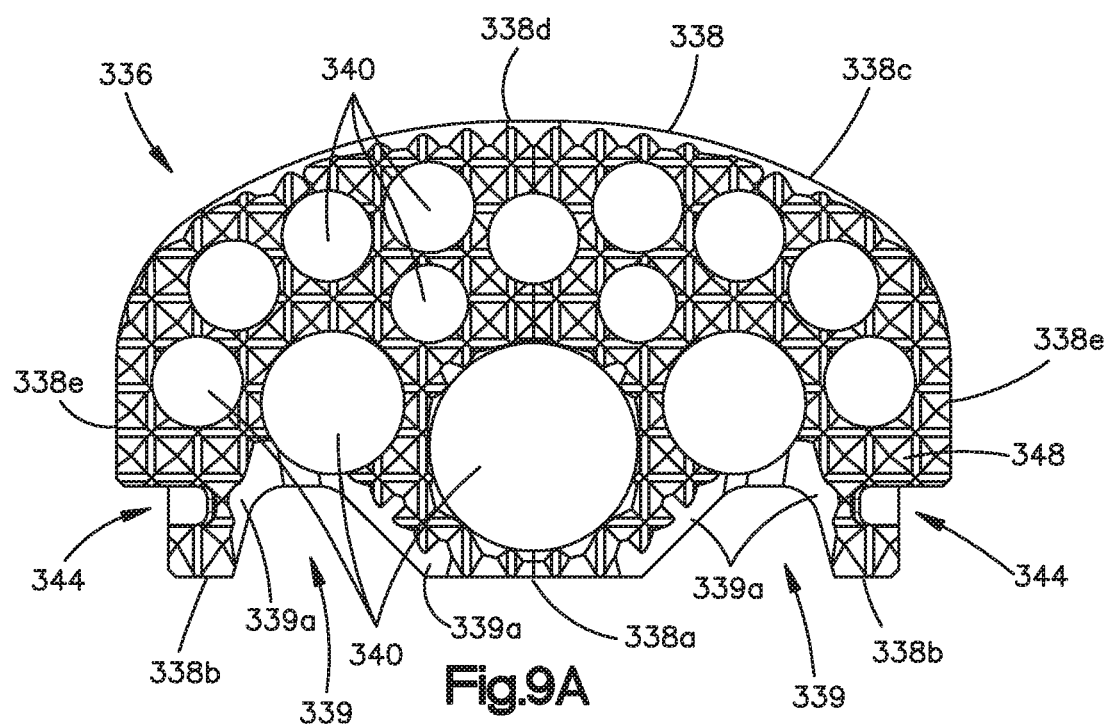
FIG. 9A is a top elevation view of an intervertebral implant spacer for use with arcuate fixation members, constructed in accordance with another alternative embodiment.
Figure 9B:
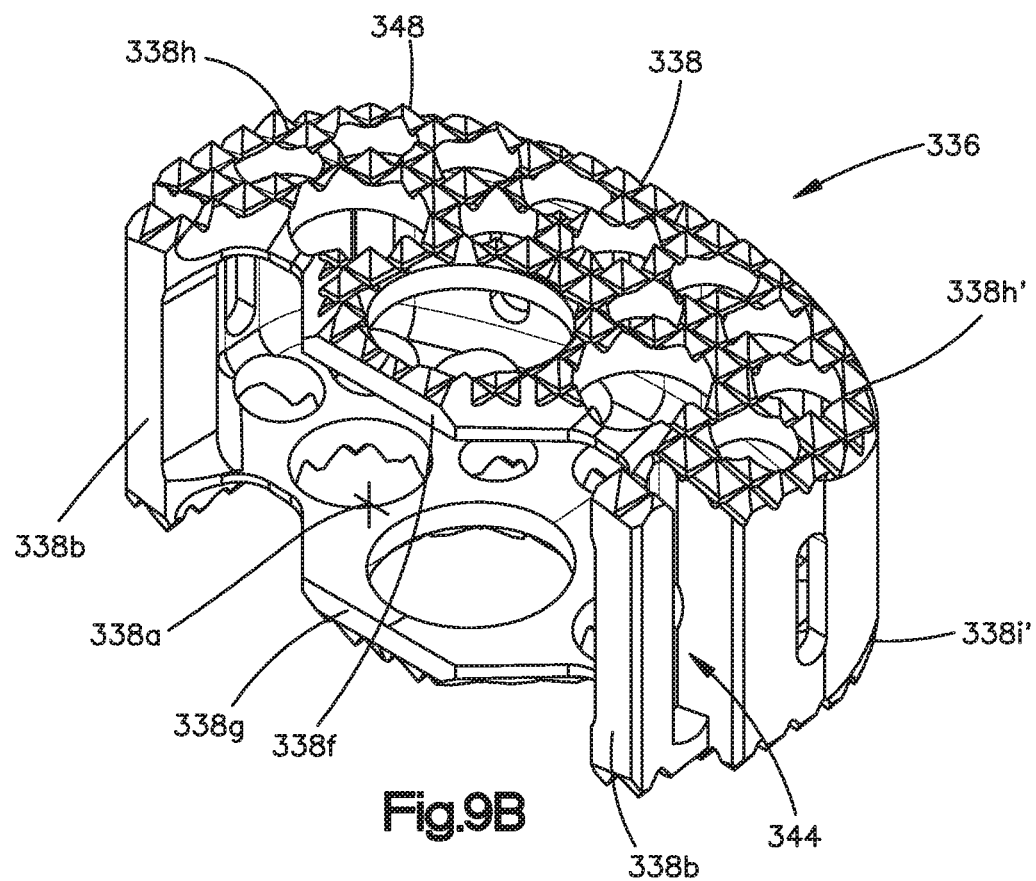
FIG. 9B is a perspective view of the intervertebral implant spacer illustrated in FIG. 9A.
Figure 9C:
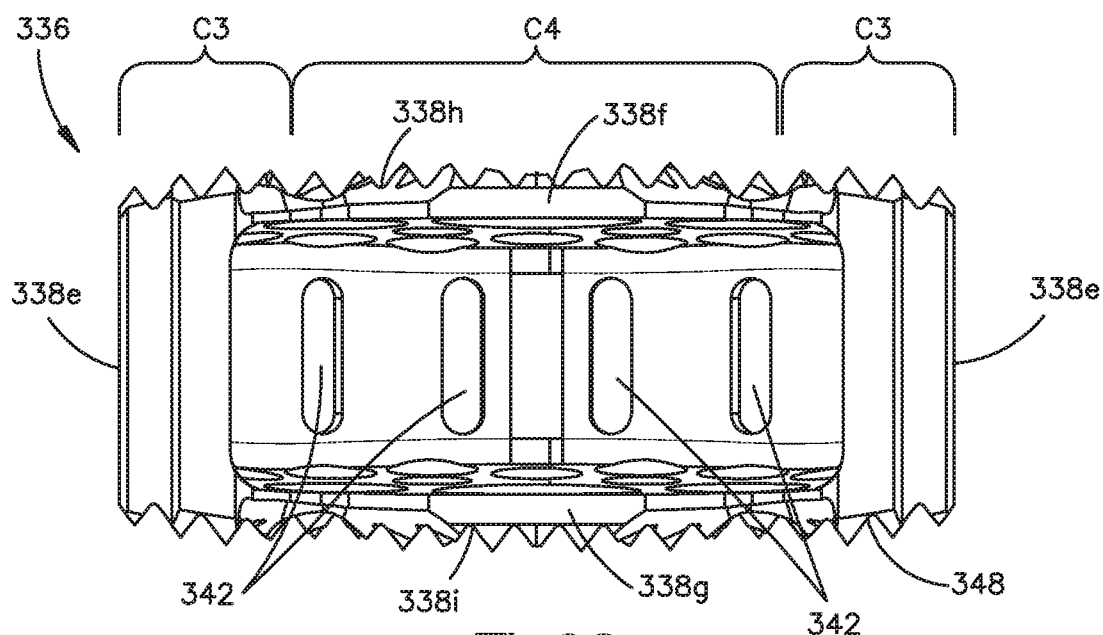
FIG. 9C is a front elevation view of the intervertebral implant spacer illustrated in FIG. 9A.
Figure 9D:
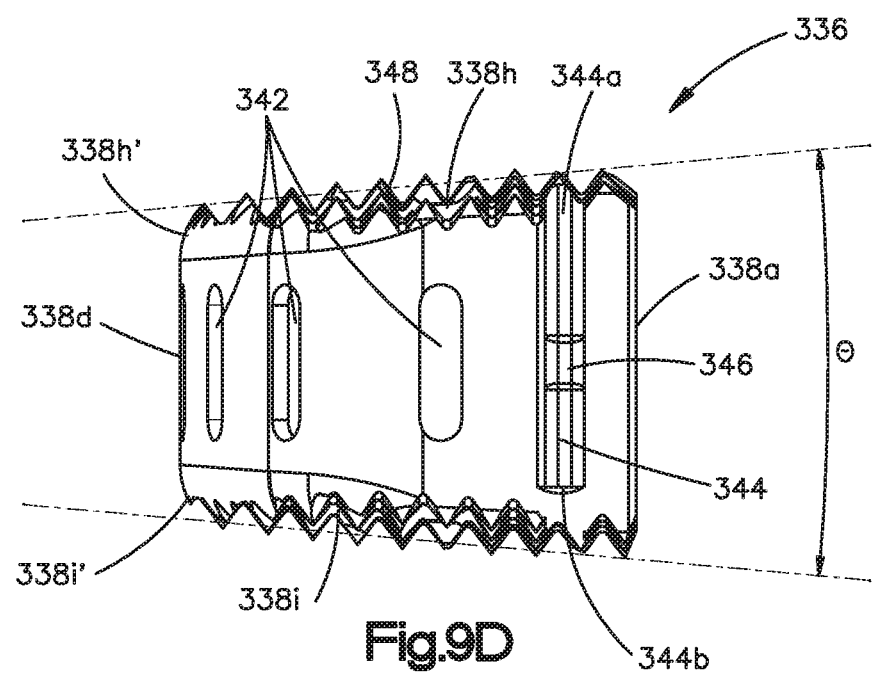
FIG. 9D is a side elevation view of the intervertebral implant spacer illustrated in FIG. 9A.
Figure 10A:
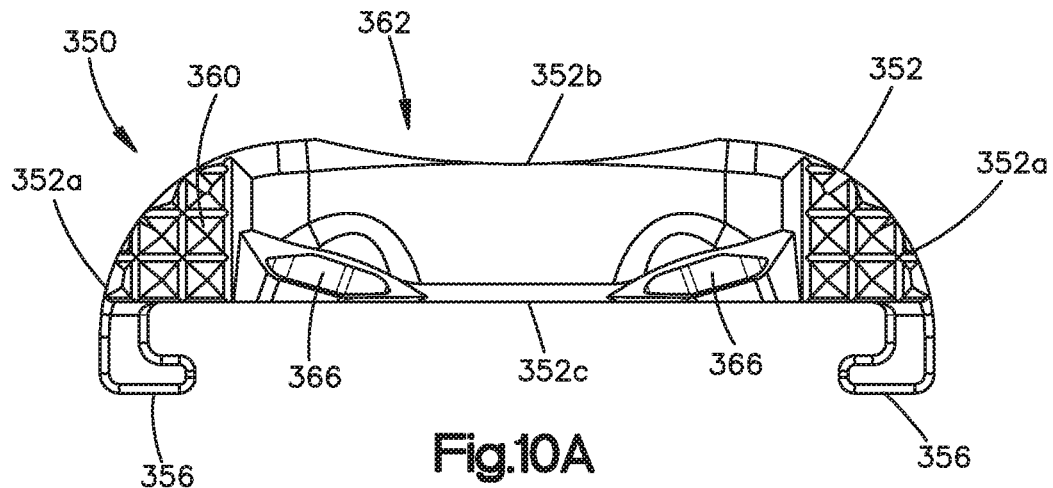
FIG. 10A is a top elevation view of an insert plate for use with the intervertebral implant spacers illustrated in FIGS. 8A-D and 9A-D.
Figure 10B:
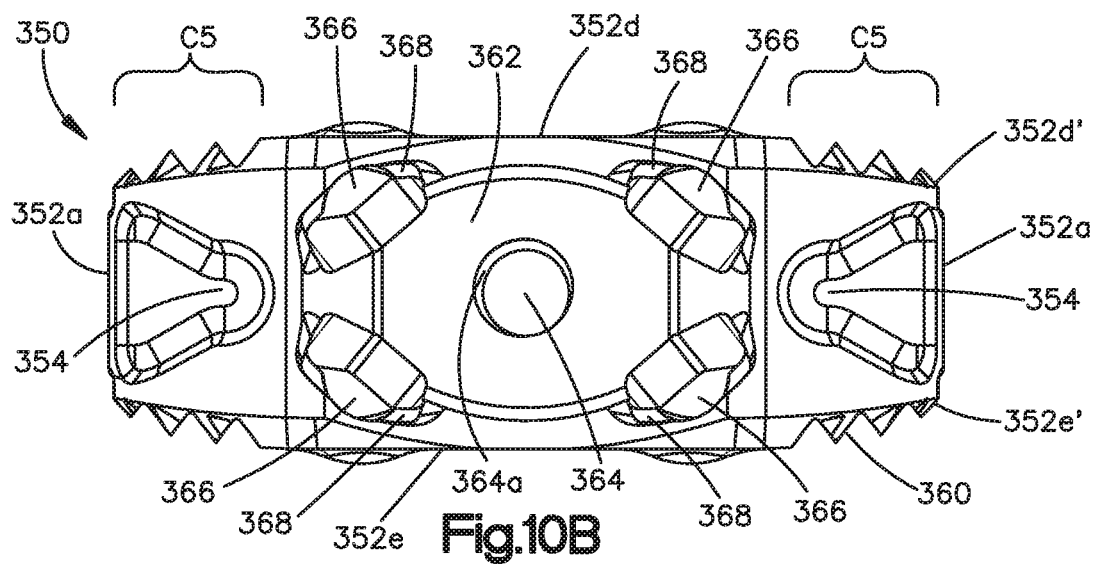
FIG. 10B is a front elevation view of the insert plate illustrated in FIG. 10A.
Figure 10C:
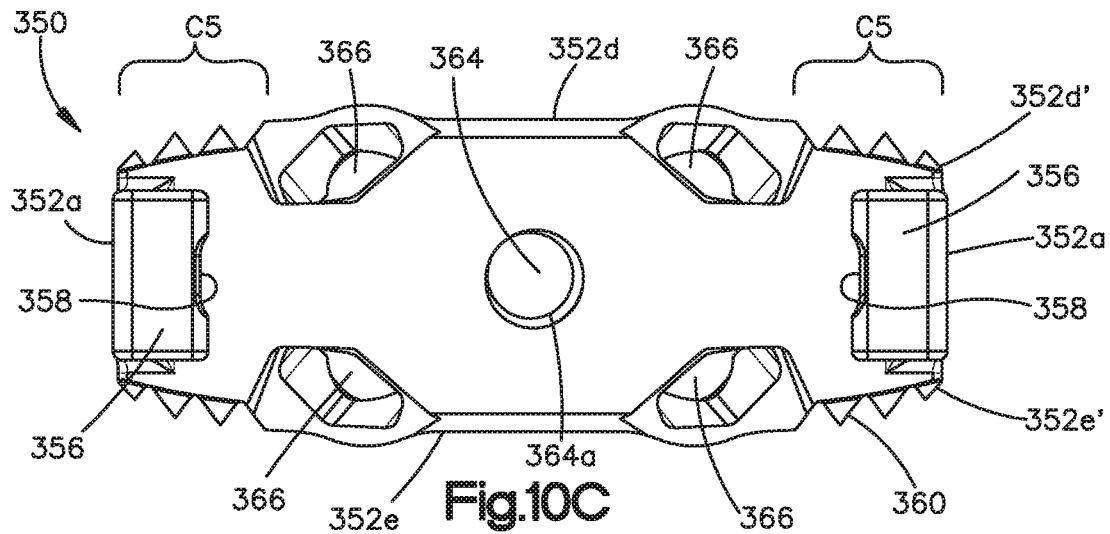
FIG. 10C is a rear elevation view of the insert plate illustrated in FIG. 10A.
Figure 10D:
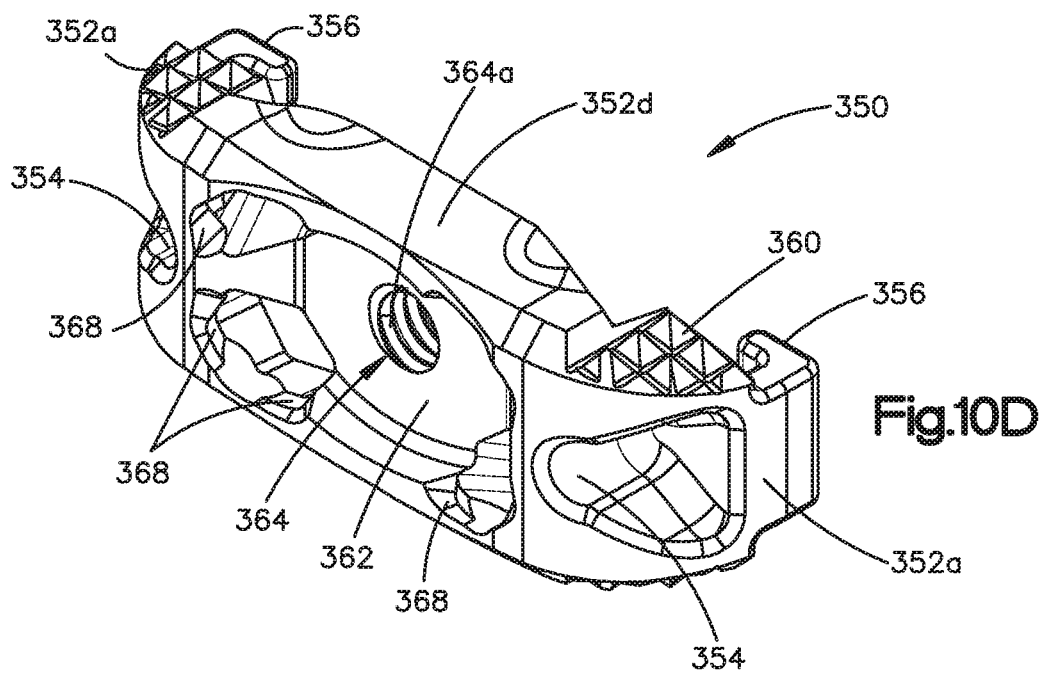
FIG. 10D is a perspective view of the insert plate illustrated in FIG. 10A.
Figure 10E:
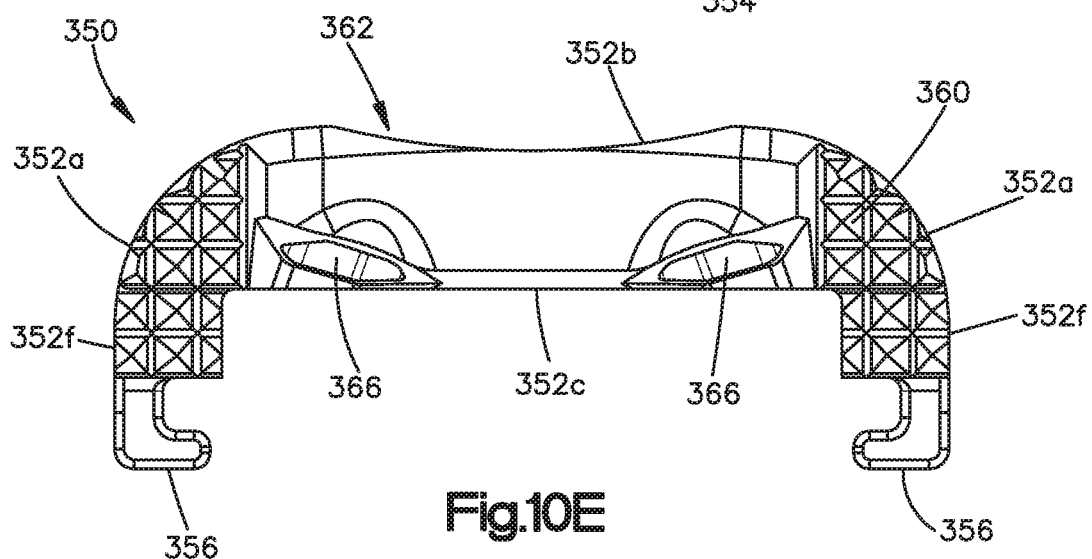
FIG. 10E is a top elevation view of the insert plate illustrated in FIG. 10A, constructed in accordance with an alternative embodiment.
Figure 10F:
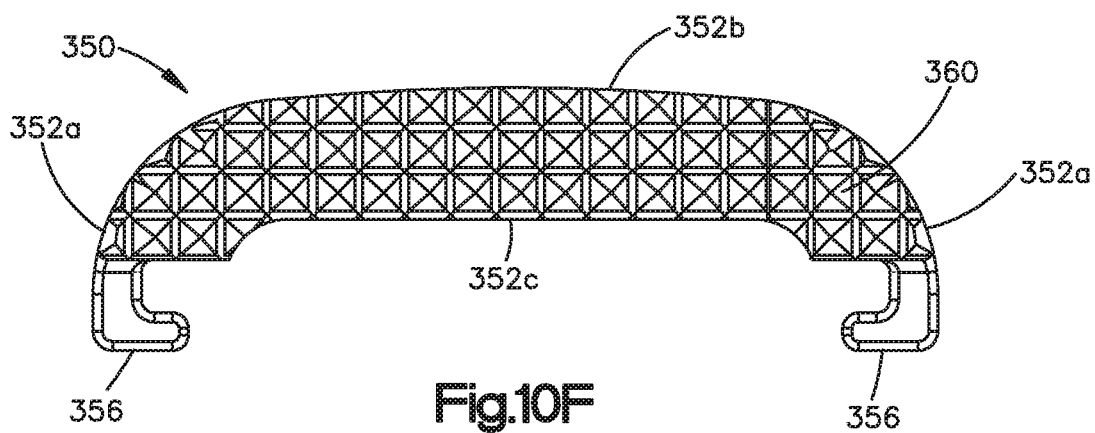
FIG. 10F is a top elevation view of the insert plate illustrated in FIG. 10A, constructed in accordance with another alternative embodiment.
Figure 11A:
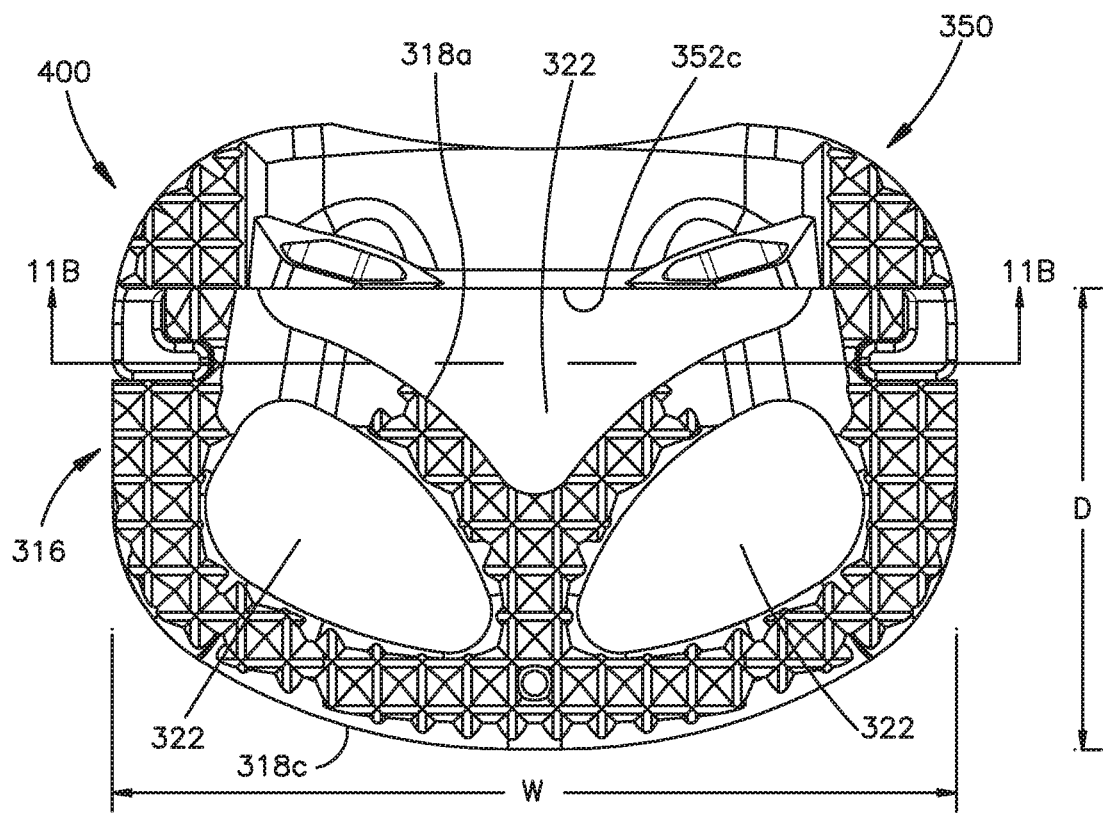
FIG. 11A is a top elevation view of an intervertebral implant constructed with an alternative embodiment of the intervertebral implant spacer illustrated in FIGS. 8A-D and the insert plate illustrated in FIGS. 10A-D.
Figure 11B:
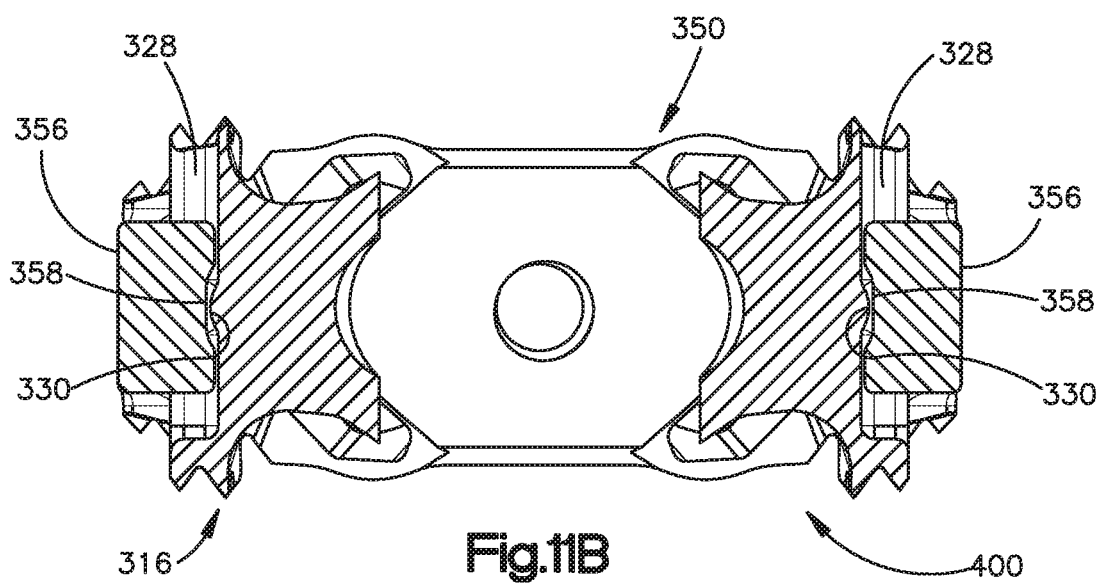
FIG. 11B is a sectional elevation view of the intervertebral implant illustrated in FIG. 11A, taken along line 11B-11B.

Referring now to FIGS. 9C-D, the illustrated embodiment of the spacer 336 has a generally wedge shaped side view profile defined by a gradual increase in height followed by a gradual decrease in height between the anterior end 338a and the posterior wall 338d, and a generally rectangular front view profile defined by a generally constant height throughout the C4 region, and gradually decreasing height throughout the C3 regions between the opposing ends of the C4 region and the side walls 338e. In alternative embodiments the height between the anterior end 338a and the posterior wall 338d of the spacer 336 may gradually decrease, may gradually increase, may have a gradual decrease followed by a gradual increase, or may be generally constant, while the height between the side walls 338e may increase and/or decrease, or may be generally constant.

The geometry of the spacer 336, for instance the geometry of the upper and lower surfaces 338h-i and/or the difference in the height of the body 338 between the anterior end 338a and the posterior wall 338d defines a lordotic angle θ of the spacer 336. The lordotic angle θ defined by the spacer 336 can be increased and/or decreased by varying the geometry of the spacer 336. For example, the lordotic angle θ defined by the illustrated spacer 336 can be increased by heightening the anterior end 338a of the spacer 336 while maintaining the height of the posterior wall 338d. In preferred embodiments, the anterior-posterior convexity defined by the upper surface 338h is increased with increasing magnitude of the lordotic angle θ, while the anterior-posterior convexity defined by the lower surface 338i is maintained. It should be appreciated that when the geometry of the spacer 336 is alternatively constructed in order to increase or decrease the lordotic angle θ defined by the spacer 336, the anterior-posterior convexity and/or the lateral convexity of the upper and/or lower surfaces 338h-i can be increased or decreased in any combination such that the upper and lower surfaces 338h-i are defined the same or differently.

Referring now to FIGS. 10A-F, alternative embodiments of the insert plate are illustrated. The insert plate, or insert 350 defines a plate having plate body, or body 352 extending between opposing plate ends 352a, the plate body 352 defining an anterior side 352b, a posterior side 352c opposite the anterior side, an upper surface 352d, and a lower surface 352e opposite the upper surface. In the illustrated embodiments, the anterior side 352b defines a curved outer periphery of the plate body 352. The plate body 352 can define one or more insert members, such as insert slots 354, the insert members configured to receive the complementary members defined on a delivery, or insertion instrument. It should be appreciated that the insert members are not limited to the illustrated insert slots 354, and that the insert members can be alternatively defined in accordance with the complementary insert members of a respective delivery instrument.

The insert plate 350 is configured to be coupled to a spacer, for instance the above-described spacers 316 or 336. Coupling members can be defined on the plate body 352, the coupling members configured to releasably mate with complementary coupling members of a spacer. For example, in the illustrated embodiments, coupling members in the form of retaining members 356 are defined on the insert plate 350, the retaining members being generally "L" shaped, so as to be slidably received in the retaining grooves 328 or 344 of the spacers 316 or 336, respectively. In the embodiments illustrated in FIGS. 10A-D and 10F, a "shallow" insert plate 350 is depicted, in which the retaining members 356 are defined on the plate ends 352a, the retaining members 356 extending outwardly from the posterior side 352c of the plate body 352. When the shallow insert plate 350 is coupled to the spacer 316 (see FIG. 11A), an aperture 322 is defined between the anterior wall 318a of the spacer body 318 of the spacer 316 and the posterior side 352c of the plate body 352 of the shallow insert plate. In the embodiment illustrated in FIG. 10E, a "deep" insert plate 350 is depicted, in which the retaining members 356 are defined at the ends of side walls 352f that extend from the plate ends 352a, the retaining members 356 extending outwardly from the ends of the side walls 352f When the deep insert plate 350 is coupled to the spacer 316, an aperture 322 is defined between the anterior wall 318a of the spacer body 318 of the spacer 316 and the posterior side 352c and side walls 352f of the plate body 352 of the shallow insert plate. The volume of the aperture 322 defined by the spacer 316 coupled to the deep insert plate 350 is greater than the volume of the aperture 322 defined by the spacer 316 coupled to the deep insert plate 350.

Interlocking members can be defined on the coupling members, the interlocking members configured to receive complementary interlocking members, such as the retaining grooves 328 or 344 defined in the spacers 316 or 336, respectively, in releasably locking engagement. For example, in the illustrated embodiments, interlocking members in the form of locking grooves 358 are defined in the ends of the retaining members 356. The locking grooves are define a height in the transverse direction, and are of sufficient height to receive the locking ridges 330 or 346 of the spacers 316 or 336, respectively, therein. In addition to locking the insert plate 350 into position with respect to a spacer 316 or 336, the interlocking members can be configured to facilitate a desired alignment in the transverse direction between the insert plate 350 and the respective spacer, as described above. In the illustrated embodiments the locking grooves 358 can define a height that is longer than the corresponding height of the locking ridges 330 or 346, in order to allow for a limited amount of translation by the insert plate 350 and the respective spacer with respect to each other.

It should be appreciated that the insert plate 350 and spacers 316 and 336 are not limited to the illustrated configurations of the coupling members and/or interlocking members. For example, the retaining grooves 328 or 344 could be defined in the insert plate 350, and the retaining members 356 could be defined on the spacers 316 or 336. Similarly, the locking ridges 330 or 346 could be defined on the retaining members 356, and the locking grooves 358 could be defined in the retaining grooves 328 or 344. It should further be appreciated that the coupling members are not limited to the illustrated structures of the retaining grooves 328 and 344 or the retaining members 356. For example, the respective orientations of the retaining grooves 328 or 344 and the retaining members 356 could be reversed with respect to the lateral direction. It should further still be appreciated that the insert plate 350 and spacers 316 and 336 are not limited to the illustrated coupling members and/or interlocking members, and that any alternative structures can be employed to couple and/or lock the spacers 316 or 336 and the insert plate 350 with respect to each other.

The upper and lower surfaces 352d-e of the plate body 352 can be configured as bone-engaging surfaces, for example by defining gripping structures thereon, such as teeth, spikes, or the like. The gripping structures can be configured to engage adjacent underlying structures, such as the endplates of adjacent vertebral bodies, when the intervertebral implant 400 is inserted into an intervertebral space. In the embodiments illustrated in FIGS. 10A-D and 10F, portions of the upper and lower surfaces 352d-e have teeth 360 defined thereon. The teeth 360 may be pyramidal, saw toothed or other similar shapes. In the embodiment illustrated in FIG. 10E, the entireties of the upper and lower surfaces 352d-e have teeth 360 defined thereon. The upper and lower edges 352d'-e' of the upper and lower surfaces 352d-e, respectively, can be rounded. Rounding the upper and lower edges 352d'-e' can facilitate easier insertion and/or removal of the insert plate 350, and thus the intervertebral implant 400, from an intervertebral space, for example by minimizing required distraction of the end plates of adjacent vertebral bodies. Distinct portions, up to an entirety of the upper and lower edges 352d'-e' can be rounded using substantially constant or varying radii of curvature.

The geometry of the upper and lower surfaces 352d-e of the plate body 352 may be defined to generally conform the insert plate 350 to the geometry of the spacers 316 or 336. For example, in the illustrated embodiments, the upper and lower surfaces 352d-e are defined as partially convex surfaces. In particular, the upper and lower surfaces 352d-e exhibit lateral convexity in the regions C5 near the plate ends 352a, the convexity on the upper and lower surfaces 352d-e being symmetric with respect to each other. The height of the insert plate 350 gradually decreases between the anterior and posterior sides 352b-c, respectively (see FIGS. 12A-B). It should be appreciated that the insert plate 350 is not limited to the illustrated geometry of the upper and lower surfaces 352d-e, and that the upper and lower surfaces 352d-e can be defined with full or partial convexity in the anterior-posterior and/or lateral directions, with full or partial concavity in the anterior-posterior and/or lateral directions, with a combination of partial convexity and concavity in the anterior-posterior and/or lateral directions, or with no curvature at all (i.e., substantially flat) in the anterior-posterior and/or lateral directions. It should further be appreciated that the regions C5 can be defined with wider or narrower widths in the lateral direction. It should further still be appreciated that the geometry of the upper and lower surfaces 352d-e can be defined either symmetrically or asymmetrically with respect to each other. It should further still be appreciated that the height of the insert plate 350 between the anterior and posterior sides 352b-c, respectively, may gradually increase, may have a gradual decrease followed by a gradual increase, may have a gradual increase followed by a gradual decrease, or may be generally constant, and that the height between the plate ends 352a may increase and/or decrease, or may be generally constant.

The anterior side 352b of the plate body 352 can define a concave recess 362, the recess configured to receive the complementary convex surface of a blocking plate, such as the blocking plate 132 described above. The insert plate 350 can also have a central bore 364 defined therethrough, the central bore 364 defining a threaded inner bore surface 364a, the threads of the inner bore surface 364a configured to engage complementary threads of a locking screw, such as the locking screw 138 described above.

The plate body 352 can also have one or more guide apertures 366 defined therethrough, the guide apertures 366 configured to slidably receive bone fixation members therein, such as the arcuate fixation members 12D, and to define insertion trajectories into underlying structures for the fixation members received therein. In the illustrated embodiments, the guide apertures 366 are defined as substantially straight guide apertures extending through the plate body 352 from within the concave recess 362 in the anterior side 352b through the posterior side 352c. The guide apertures 366 can have substantially uniform cross sectional geometries that are defined to substantially conform to the cross sectional geometry of the intermediate portion 300c of the body 300 of the arcuate fixation member 12D.

The guide apertures 366 and/or the arcuate fixation members 12D can be configured to releasably lock respective arcuate fixation members 12D in inserted positions within the guide apertures 366. For example, in the illustrated embodiments, recessed ledges 368 are defined in the surface of the concave recess 362 around a portion of the perimeter of each of the guide apertures 366, the recessed ledges 368 configured to receive the lower surfaces 304b of the heads 304 of respective arcuate fixation members 12D when the arcuate fixation members 12D are inserted into respective guide apertures 366. One or more surfaces within the recessed ledges 368 can be configured to engage with complementary tapered surfaces defined on the heads 304 of respective arcuate fixation members 12D, for instance surfaces 304c, thereby locking the arcuate fixation members 12D in respective inserted positions. In an alternative embodiment, the cross sectional geometries of the guide apertures 366 can be tapered between the anterior and posterior sides 352b-c of the plate body 352, such that the arcuate fixation members 12D are press fit within the guide apertures 366 as they are inserted. Of course the arcuate fixation members 12D and/or the guide apertures 366 can be configured such that no locking affect is imparted therebetween. It should be appreciated that the above-described blocking plate 132 and locking screw 138 can be employed to secure the arcuate fixation members 12D within inserted positions in the guide apertures, whether or not the arcuate fixation members 12D and/or the guide apertures 366 are configured to releasably lock with respect to each other.

The guide apertures 366 can be disposed about the central bore 364 at any desired locations and can define any insertion trajectories as appropriate. In the illustrated embodiments, the guide apertures 366 are defined in opposing quadrants around the central bore 364, with two guide apertures 366 located near the upper surface 352d and defining two generally outward and cranial insertion trajectories, and two guide apertures 366 located near the lower surface 352e and defining two generally outward and caudal insertion trajectories. It should be appreciated that the insert plate 350 is not limited to the illustrated configuration of guide aperture 366 locations and insertion trajectories, and that the insert plate 350 can be differently configured with any number of guide apertures 366 defined at any locations on the plate body 352 and having any insertion trajectories. It should further be appreciated that the guide apertures 366 can be straight, curved along one or more locations between the anterior and posterior sides 352b-c, respectively, or any combination thereof.

Referring now to FIGS. 11A-12C, an example embodiment of an intervertebral implant 400 constructed from components of the intervertebral implant system 100 is illustrated. In particular, the intervertebral implant 400 includes an insert plate 350 coupled to a spacer 316. The intervertebral implant 400 can further include one or more arcuate fixation members 12D, a blocking plate 132, and/or a locking screw 138 (see FIGS. 14A-B), for example in accordance with the insert plate 350 provided. It should be appreciated that the intervertebral implant 400 can be alternatively constructed with the spacer 336, that the insert plate 350 can be provided as a shallow insert plate 350 or a deep insert plate 350 as described above, and that the insert plate 350 can be constructed with or without the guide apertures 366. In the illustrated embodiment, the spacer 316, and in particular the outer wall 318c, is constructed so that the width W of the spacer 316 in the lateral direction substantially conforms to the width of the insert plate 350 in the lateral direction. The insert plate 350 coupled to the spacer 316 in the illustrated embodiment is a shallow insert plate 350, as described above. When coupled to each other in an assembled configuration, the spacer 316 and the insert plate 350 define a "footprint" of the intervertebral implant 400, the footprint referring to the shape of the outer periphery of the intervertebral implant 400 as defined by the outer wall 318c of the spacer 316 and the anterior side 352b of the insert plate 350.

Figure 12A:
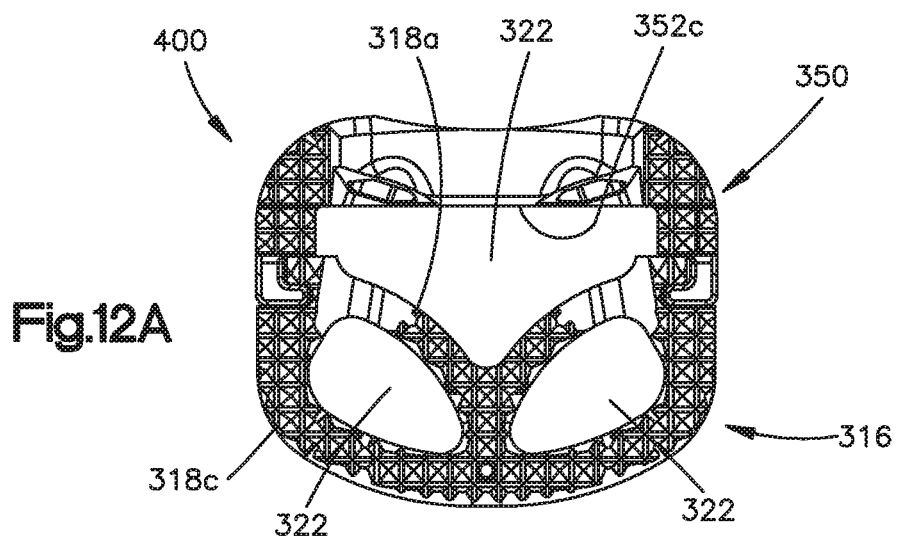
FIG. 12A is a top elevation view of the intervertebral implant illustrated in FIG. 11A, constructed in accordance with an alternative embodiment.
Figure 12B:
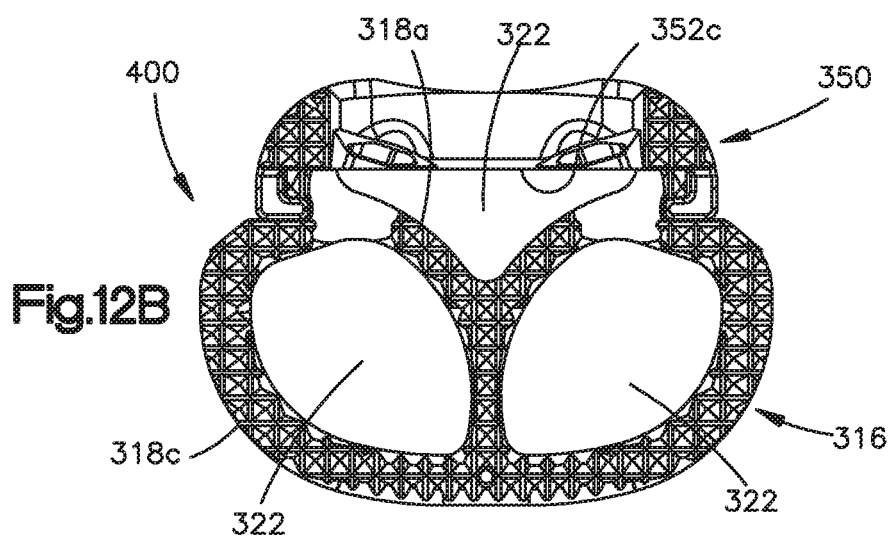
FIG. 12B is a top elevation view of the intervertebral implant illustrated in FIG. 11A, constructed in accordance with another alternative embodiment.
Figure 12C:
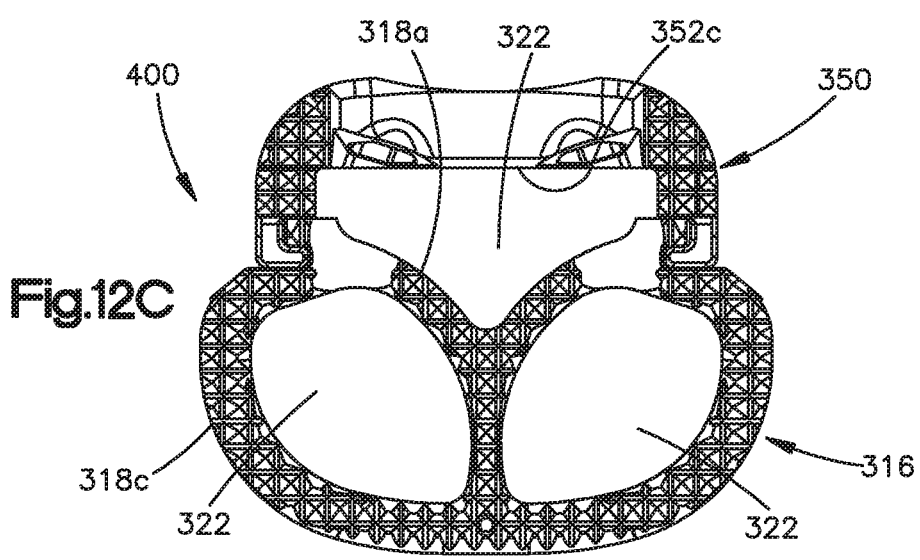
FIG. 12C is a top elevation view of the intervertebral implant illustrated in FIG. 11A, constructed in accordance with still another alternative embodiment.

It should be appreciated that the intervertebral implant 400 is not limited to the illustrated footprint, and that the spacer 316 and/or the insert plate 350 can be differently constructed to define alternative footprints of the intervertebral implant 400. For example, the deep insert plate 350, described above, can be coupled to the spacer 316 in lieu of the shallow insert plate 350, defining an intervertebral implant 400 having a larger footprint than the footprint defined by the shallow insert plate 350 coupled to the spacer 316 (see FIG. 12A). Additionally, when the deep insert plate 350 is coupled to the spacer 316, the aperture 322 defined by the anterior wall 318a of the spacer 316 and the posterior side 352c of the insert plate 350 is larger than the equivalent aperture 322 defined when the shallow insert plate 350 is coupled to the spacer 316. The spacer 316 can also be differently constructed, for example by defining the outer wall 318c with alternative widths W of the spacer 316 in the lateral direction and/or depths D of the spacer 316 in the anterior-posterior direction. For instance, the spacer 316 depicted in FIGS. 12B-C has a greater width and depth than the spacer 316 depicted in FIGS. 11A and 12A, thereby defining intervertebral implants 400 with larger footprints when coupled to the shallow or deep insert plates 350, as depicted in FIGS. 12B-C, respectively. It should be appreciated that the spacer 336 can similarly be differently constructed with varying widths and/or depths, thereby defining intervertebral implants 400 with differently sized footprints when coupled to the shallow or deep insert plates 350.

Figure 13A:
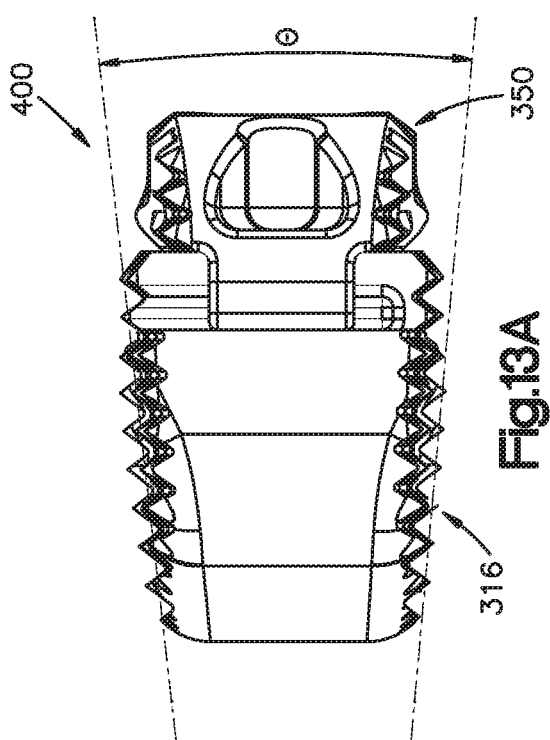
FIG. 13A is a side elevation view of an intervertebral implant constructed in accordance with an embodiment.
Figure 13B:
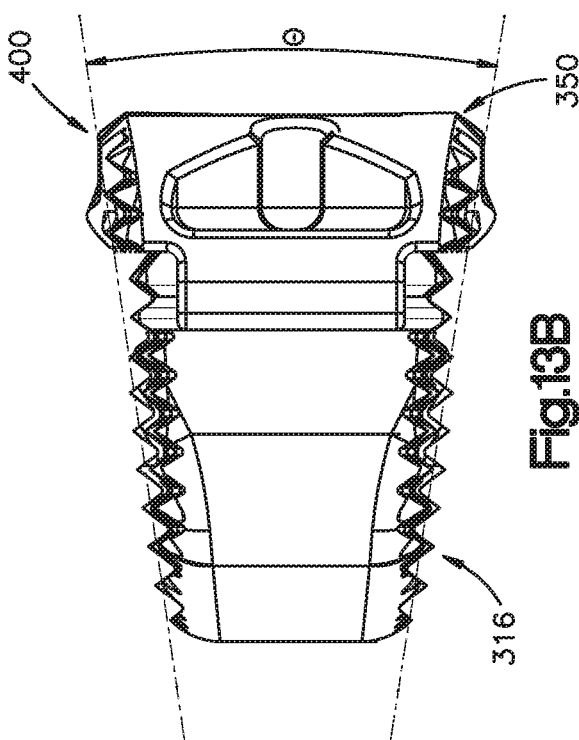
FIG. 13B is a side elevation view of the intervertebral implant illustrated in FIG. 12A, constructed in accordance with another embodiment.

Referring now to FIGS. 13A-B, in addition to providing for the construction of intervertebral implants 400 defining varying footprints, the components of the intervertebral implant system 100 also provide for the construction of intervertebral implants 400 defining varying lordotic angles. The lordotic angle θ of an intervertebral implant 400 can be defined by the geometry of its component parts, such as the surface geometry of the components and/or the height of the components. In the embodiment illustrated in FIG. 13A, a spacer 316 is coupled to an insert plate 350 having a height that is shorter than the height of the spacer 316 at the ends 318b of the anterior wall 318a. The lordotic angle θ of the intervertebral implant 400 is defined by the spacer 316. In an alternative embodiment illustrated in FIG. 13B, the spacer 316 is identical to the spacer 316 used in constructing the intervertebral implant 400 depicted in FIG. 13A, but is coupled to an insert plate 350 having a height that is taller than the height of the spacer 316 at the ends 318b of the anterior wall 318a. The increased height of the insert plate 350 produces a corresponding increase in the magnitude of the lordotic angle θ of the intervertebral implant 400. It should be appreciated that the lordotic angle defined by intervertebral implants 400 constructed using the spacer 336 can similarly be varied based upon the height of the insert plate 350 coupled thereto. It should further be appreciated that the spacers 316 and/or 336 can be differently constructed with varying heights, thereby defining intervertebral implants 400 with different lordotic angles when coupled to identical insert plates 350.

Figure 14A:
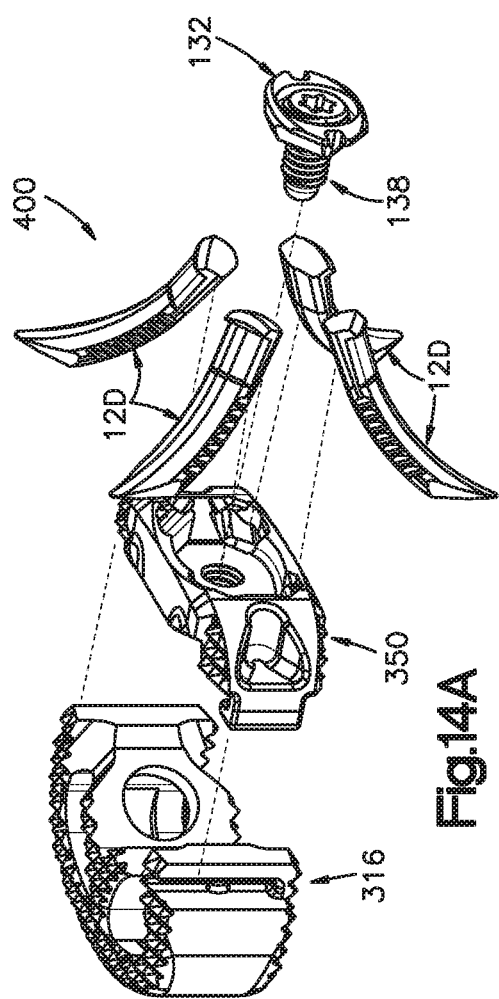
FIG. 14A is an exploded view of an intervertebral implant constructed from the intervertebral implant system components illustrated in FIGS. 7A-8D and 10A-D.
Figure 14B:
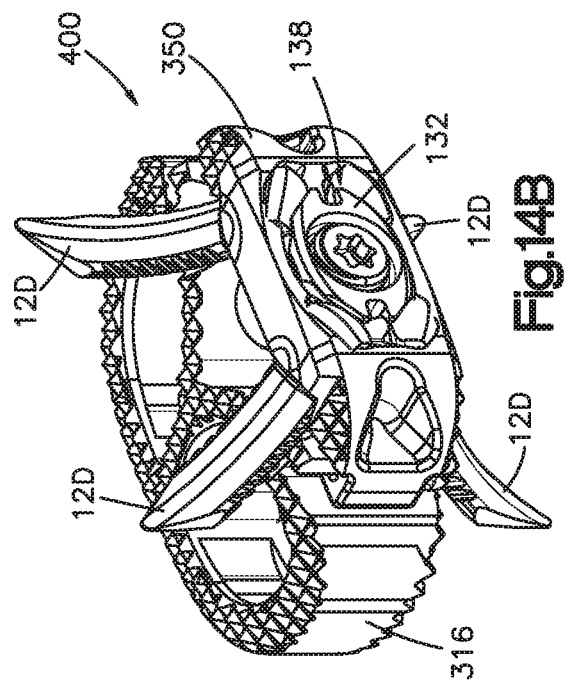
FIG. 14B is a perspective view of the intervertebral implant illustrated in FIG. 14A, in an assembled configuration.

Referring now to FIGS. 14A-B, an example intervertebral implant 400 is illustrated in an exploded view containing selected components of the intervertebral implant system 100, and in an assembled configuration after being inserted into an intervertebral space, respectively. The characteristics of the assembled intervertebral implant 400, for instance the footprint and/or lordotic angle defined thereby, can be tailored when selecting the individual components, for example in accordance with region of the spine where the intervertebral implant 400 will be inserted, particular patient anatomy, and the like. Thus, the intervertebral implant system 100 can be described as a modular intervertebral implant system 100 that allows a surgeon to construct a patient specific intervertebral implant 400. In the illustrated example, the spacer 316 and insert plate 350 can be selected based upon the desired footprint and/or or lordotic angle that will be defined by the intervertebral implant. The quantity and length of arcuate fixation members 12C and/or 12D can also be selected.

Once the components of the intervertebral implant system 100 have been selected, the spacer can be coupled to the insert plate by inserting the retaining members of the insert plate into the retaining grooves on the spacer and advancing the retaining members until the locking ridges are received in the locking grooves. The intervertebral implant 400 can then be filled with bone growth inducing substances as described above and inserted into an intervertebral space between adjacent vertebral bodies using an insertion, or delivery instrument (not shown). The arcuate fixation members can then be inserted into the guide apertures and driven into place within the adjacent vertebral bodies. Once the arcuate fixation members are inserted, a blocking plate can be disposed into the concave recess in the insert plate and a locking screw can be driven through the blocking plate and into the insert plate, thereby securing the intervertebral implant in an assembled and inserted configuration.

It should be appreciated that a variety of kits can be provided that contain one or more components of the intervertebral implant system 100. The components of the kits may be configured the same or differently. For example, within a single kit, arcuate fixation members 12C and/or 12D may be provided that have different lengths, different radii of curvature, differing head configurations, differing cross sectional geometries, and so on, depending for example on the type of procedure being performed by a surgeon, or on the particular anatomies of individual patients. The kits may also be configured differently with respect to which components of the intervertebral implant system 100 are included in the kits. For example, a kit for the intervertebral implant system 100 may include arcuate fixation members 12C and/or 12D of different lengths, radii of curvature, and/or features, and may include one or more of spacers 108, 316 and/or 336 having different heights, perimeter geometries, or surface geometries, or defining different lordotic angles, insert plates 116 or 350 having different heights, perimeter geometries, surface geometries, and guide apertures, blocking plates 132, or locking screws 138.

Although arcuate fixation members and the other components of the intervertebral implant system 100 have been described herein with reference to preferred embodiments or preferred methods, it should be understood that the words which have been used herein are words of description and illustration, rather than words of limitation. For example, it should be noted that although the intervertebral implant system 100 has been described herein with reference to particular structure, methods, and/or embodiments, the scope of the instant disclosure is not intended to be limited to those particulars, but rather is meant to extend to all structures, methods, and/or uses of the intervertebral implant system 100. Those skilled in the relevant art, having the benefit of the teachings of this specification, may effect numerous modifications to the intervertebral implant system 100 as described herein, and changes may be made without departing from the scope and spirit of the instant disclosure, for instance as recited in the appended claims.

What is claimed:

1. A method for fixing an intervertebral implant in an intervertebral space defined between an upper vertebral body and a lower vertebral body, the method comprising the steps of:
    inserting a spacer body of the intervertebral implant into the intervertebral space so that upper and lower bone-engaging surfaces of the spacer body engage the upper and lower vertebral bodies, respectively, wherein a fixation plate of the intervertebral implant is coupled to the spacer body, wherein the fixation plate comprises retaining members which are received in complementary retaining grooves of the spacer body to couple the fixation plate to the spacer body opposite a posterior wall of the spacer body, the fixation plate defining a plurality of guide apertures extending therethrough for receiving a plurality of curved bone fixation members, wherein the spacer body includes a pair of side walls that extend between the posterior wall and the fixation plate, the spacer body defines an aperture that extends from the lower bone-engaging surface to the upper bone-engaging surface and extends between the pair of side walls along a first direction and extends between the posterior wall and the fixation plate along a second direction that is perpendicular to the first direction,
    the posterior wall defining an inner surface that faces toward the fixation plate, the inner surface defining at least one cavity that is open to the aperture, the at least one cavity defining a recessed surface that is positioned intermediate the inner surface and an outer surface of the posterior wall;
    disposing bone growth inducing substance into the aperture such that at least some of the bone growth inducing substance extends within the at least one cavity; and
    inserting a plurality of curved bone fixation members into respective ones of the plurality of guide apertures such that each curved bone fixation member fixes the intervertebral implant to one of the upper and lower vertebral bodies.

2. The method of claim 1, wherein the disposing step comprises packing the bone growth inducing substance into the aperture prior to the inserting step.

3. The method of claim 1, wherein the bone growth inducing substance is disposed into the aperture to fill the aperture and allowing boney ingrowth into the at least one cavity.

4. The method of claim 1, wherein the at least one cavity is elongate along the first direction.

5. The method of claim 1, wherein the at least one cavity comprises a plurality of cavities.

6. The method of claim 1, wherein at least one of the curved bone fixation members of the plurality of curved bone fixation members is rotationally fixed in a respective one of the plurality of guide apertures as the at least one curved bone fixation member is inserted into engagement with one of the upper and lower vertebral bodies.

7. The method of claim 6, wherein the at least one curved bone fixation member is guided along an insertion trajectory through the one of the upper and lower vertebral bodies, and wherein a guidance member disposed at least partially along a distal end of the at least one curved bone fixation member facilitates the guiding.

8. The method of claim 7, wherein the guidance member comprises a keel extending from the distal end, at least one wing disposed adjacent the keel, and a flute disposed between the keel and the at least one wing.

9. The method of claim 8, wherein the guidance member further comprises a second wing disposed adjacent the keel, such that the keel is disposed between the wings.

10. The method of claim 8, wherein the flute extends substantially parallel to the insertion trajectory.

11. The method of claim 7, further comprising driving a curved intermediate portion of the at least one curved bone fixation member, the curved intermediate portion extending between a proximal end and the distal end of the at least one curved bone fixation member, wherein the driving step comprises sliding the curved intermediate portion through the respective one of the plurality of guide apertures such that a cross-sectional shape of the curved intermediate portion resides within a conforming cross-sectional shape of the respective one of the plurality of guide apertures.

12. The method of claim 7, wherein a tapered tip of the at least one curved bone fixation member cuts into the one of the upper and lower vertebral bodies during insertion.

13. The method of claim 6, further comprising positioning at least one blocking member with respect to the plurality of curved bone fixation members such that a portion thereof extends behind a proximal end of the at least one curved bone fixation member, thereby blocking the at least one curved bone fixation member from backing out of the respective one of the plurality of guide apertures.

14. A method for implanting an intervertebral implant in an intervertebral space, the method comprising the steps of:
    inserting a spacer body of the intervertebral implant into the intervertebral space so that upper and lower bone-engaging surfaces of the spacer body engage upper and lower vertebral bodies, respectively,
    wherein a fixation plate of the intervertebral implant is coupled to the spacer body, the fixation plate comprises retaining members which are received in complementary retaining grooves of the spacer body to couple the fixation plate to an anterior wall of the spacer body opposite a posterior wall of the spacer body, the fixation plate defining a plurality of guide apertures extending therethrough for receiving a plurality of bone fixation members, the spacer body includes a pair of side walls that are spaced from each other along a first direction, the sidewalls extending between the anterior and posterior walls along a second direction that is perpendicular to the first direction, the spacer body defining a first aperture and a second aperture that each extend from the lower bone-engaging surface to the upper bone-engaging surface along a third direction that is perpendicular to the first and second directions, wherein the first and second apertures are located between the side walls along the first direction and between the anterior and posterior walls along the second direction, the spacer body further defining an inner wall that extends between the anterior and posterior walls along the second direction and separates the first and second apertures, disposing bone growth inducing substance into the first and second apertures such that at least some of the bone growth inducing substance extends within first and second cavities defined within an inner surface of the posterior wall, wherein the first cavity is open to the first aperture and the second cavity is open to the second aperture, and each of the first and second cavities defines a recessed surface positioned intermediate the inner surface and an outer surface of the posterior wall; and inserting a plurality of bone fixation members into respective ones of the plurality of guide apertures such that each bone fixation member fixes the intervertebral implant to one of the upper and lower vertebral bodies.

15. The method of claim 14, wherein the disposing step comprises packing the bone growth inducing substance into the first and second apertures prior to the inserting step, and wherein the bone growth inducing substance is disposed into the first and second apertures to fill the first and second apertures and allow boney ingrowth into the first and second cavities.

16. The method of claim 14, wherein at least one of the bone fixation members of the plurality of bone fixation members is rotationally fixed in a respective one of the plurality of guide apertures as the at least one bone fixation member is inserted into engagement with one of the upper and lower vertebral bodies.

17. The method of claim 16, wherein the plurality of bone fixation members are each curved bone fixation members.

18. The method of claim 17, wherein the at least one bone fixation member is guided along an insertion trajectory through the one of the upper and lower vertebral bodies, and wherein a guidance member disposed at least partially along a distal end of the at least one bone fixation member facilitates the guiding.

19. The method of claim 18, wherein the guidance member comprises a keel extending from the distal end, at least one wing disposed adjacent the keel, and a flute disposed between the keel and the at least one wing.

\* \* \* \* \*